US008889120B2

(12) United States Patent
Sako et al.

(10) Patent No.: US 8,889,120 B2
(45) Date of Patent: Nov. 18, 2014

(54) METHOD FOR CONSTRUCTING NOVEL BACTERIUM BELONGING TO THE GENUS BIFIDOBACTERIUM

(75) Inventors: Tomoyuki Sako, Minato-ku (JP); Mika Miura, Minato-ku (JP); Yasuhisa Shimakawa, Minato-ku (JP); Koji Miyazaki, Minato-ku (JP); Junji Fujimoto, Minato-ku (JP); Koichi Watanabe, Minato-ku (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 13/577,511

(22) PCT Filed: Feb. 21, 2011

(86) PCT No.: PCT/JP2011/053737
§ 371 (c)(1),
(2), (4) Date: Aug. 7, 2012

(87) PCT Pub. No.: WO2011/105335
PCT Pub. Date: Sep. 1, 2011

(65) Prior Publication Data
US 2012/0329059 A1 Dec. 27, 2012

(30) Foreign Application Priority Data
Feb. 24, 2010 (JP) ................... 2010-039212
Jun. 16, 2010 (JP) ................... 2010-136792

(51) Int. Cl.
C12R 1/01 (2006.01)
A23L 2/52 (2006.01)
C12N 1/36 (2006.01)
A23L 1/30 (2006.01)
A23C 9/123 (2006.01)
C12Q 1/68 (2006.01)

(52) U.S. Cl.
CPC ............... *C12R 1/01* (2013.01); *A23Y 2300/29* (2013.01); *A23Y 2300/25* (2013.01); *A23L 2/52* (2013.01); *A23Y 2300/00* (2013.01); *C12N 1/36* (2013.01); *A23L 1/3014* (2013.01); *A23Y 2240/41* (2013.01); *A23Y 2220/03* (2013.01); *A23C 9/1234* (2013.01); *A23C 9/1236* (2013.01); *C12Q 1/689* (2013.01)
USPC ........ 424/93.45; 424/93.4; 424/93.1; 426/61; 426/43; 426/590; 426/52; 426/34; 435/6.12; 435/41; 435/243

(58) Field of Classification Search
CPC ... A61K 35/745; A61K 2300/00; A61K 8/99; A61K 9/0095; A61K 2035/115; A61K 35/66; A23V 2002/00; A23V 2200/3204; A23V 2200/30; A23L 1/3014; A23L 1/0345; C12N 1/20; C12N 1/04; C12N 15/746; A23C 9/1234; A23C 19/0323; A23C 11/106; A23C 19/032; A23C 17/02; A23C 15/123
USPC ............... 424/93.4, 93.1, 93.45; 435/6.12, 41, 435/243; 426/61, 43, 590, 52, 34, 252.1, 426/252.9
See application file for complete search history.

(56) References Cited

U.S. PATENT DOCUMENTS

| 4,087,559 A | 5/1978 | Mutai et al. |
| 4,734,361 A | 3/1988 | Murao et al. |
| 5,711,977 A | 1/1998 | Yang et al. |
| 7,510,735 B2 * | 3/2009 | Shimakawa et al. ............ 426/42 |
| 2004/0052902 A1 | 3/2004 | Shimakawa et al. |
| 2005/0031735 A1 | 2/2005 | Serata et al. |
| 2007/0150978 A1 | 6/2007 | Byrum |
| 2009/0252709 A1 | 10/2009 | Nose et al. |

FOREIGN PATENT DOCUMENTS

| CN | 1248146 A | 3/2000 |
| CN | 1269827 A | 10/2000 |
| CN | 101228262 A | 7/2008 |
| EP | 0 974 268 A1 | 1/2000 |
| EP | 1 010 753 A1 | 6/2000 |
| EP | 1 443 105 A1 | 8/2004 |
| EP | 1443105 A1 * | 8/2004 |
| EP | 1 930 407 A1 | 6/2008 |
| JP | 61 19220 | 5/1986 |
| JP | 62 628 | 1/1987 |
| JP | 4-320642 A | 11/1992 |
| JP | 9 322762 | 12/1997 |
| JP | 11-75828 A | 3/1999 |

(Continued)

OTHER PUBLICATIONS

Combined Chinese Office Action and Search Report issued Apr. 3, 2013 in Patent Application No. 201180010882.4 with English Translation of Summary and English Translation of Category of Cited Documents.
New Zealand Further Examination Report issued Aug. 19, 2013, in Patent Application No. 601532.
"Roseobacter denitrificans OCh 114, complete genome", GenBank CP000362.1,(author W. D. Swingley, et al., ), Nucleotide—NCBI, http://www.ncbi.nlm.nih.gov, Jun. 22, 2006, 460 pages.

(Continued)

*Primary Examiner* — Ja'Na Hines
*Assistant Examiner* — Mary Lyons
(74) *Attorney, Agent, or Firm* — Oblon, Spivak, McClelland, Maier & Neustadt, L.L.P.

(57) ABSTRACT

A method for producing bacteria belonging to the genus *Bifidobacterium* having excellent viability even under various conditions with different environmental factors, novel bacteria belonging to the genus *Bifidobacterium* obtained by the method, and a method for detecting the bacteria are provided. By subculturing and storing bacteria belonging to the genus *Bifidobacterium* alternately in systems under conditions with different environmental factors, the bacteria belonging to the genus *Bifidobacterium* exhibiting excellent viability under all the conditions used for the alternate subculturing and storing can be produced.

8 Claims, 5 Drawing Sheets

(56) References Cited

FOREIGN PATENT DOCUMENTS

| JP | 11 75830 | 3/1999 |
|---|---|---|
| JP | 2922013 | 7/1999 |
| WO | 02 061118 | 8/2002 |
| WO | 03 040350 | 5/2003 |

OTHER PUBLICATIONS

"Predicted: *Canis lupus* familiaris REST corepressor 2, transcript variant 1 (RCOR2), mRNA", (Nucleotide), XM_540889.3, http://www.ncbi.nlm.nih.gov, Jan. 4, 2005, 2 pages.

Extended European Search Report issued Feb. 19, 2013, in European Patent Application No. 11747296.9.

C. Monnet, et al., "Improvement of the Resistance of *Lactobacillus delbrueckii* ssp. bulgaricus to Freezing by Natural Selection", Journal of Dairy Science, American Dairy Science Association, vol. 86, No. 10, XP-026982873, Oct. 1, 2003, pp. 3048-3053.

"Mus musculus BAC clone RP24-441C24 from chromosome 2, complete sequence", Database GenBank, [online], Accession No. AC129302, <http://www.ncbi.nlm.nih.gov/nuccore/AC129302>, Nov. 13, 2003 uploaded, [retrieved on Feb. 7, 2014], 1page.

Office Action issued Feb. 18, 2014, in Japanese Patent Application No. 2012-501772 with partial English translation.

International Search Report Issued Mar. 22, 2011 in PCT/JP11/53737 Filed Feb. 21, 2011.

\* cited by examiner

FIG. 1

```
AGCCAGTTTC GAGGTATGGC CGGTACTACC ACGCGAACCC GGGCGGTGGA ACAGCCTCCA   60
AAGGGTGAAG GTGTTCATCG CTTGCCTCCC GCGTTGATGT CGTGACCGAC GGCTGCAGCA  120
GCGTTGGCGT CGGCATCCGG CTGATGCAGC CTACCGTCCT GCATCATTAC GGTTCGGCCA  180
CAGAAGCCAG CGACGTTGGG ATCGTGCGTT ACGACCACTA CGGCAGCGCC GTTATCACGC  240
GCTGCGGCCA TCAGGATGCC CATCACCTCA CGTCCGGTGG TCTGATCGAG GGCACCGGTC  300
GGTTCGTCGG CGAATACCAC GGCTGGTTTC ACGGCGAGCG CACGGGCGAT GGCGATGCGC  360
TGCATCTGAC CGCCGCTCAT CTCCCCCGGC CGGTTATTGG CGAGGGCACG AAGGCCCATG  420
CGTTCCAGCC AGAGAATCGC GGTGTCGGTG GCGGTGCGGT ATGGCATGCC GTCGAGCATC  480
ATCGGCAGTG CGATATTTTC GACTGCCGGC AATTCGGGAA GCAGCTGGCC GGATTGGAAG  540
ACAAAACCGA AAGCGTTGCG GCGCAGCTTG GTGCGGCCGG CATCGCTCAT GGCATCCAGA  600
TTCGAGCCAC GGAAGGTCAC TGTGCCGGCG GTCGGCTTGA TGATGCCGGC GAGCGCGTGC  660
AGCAGCGTGG ACTTGCCGGA GCCAGACGGG CCCATGACAG CAACCGTCTC ACCCTCACCC  720
AATGCGAAGC TCACGTGGTT CAGGGCAAGT GTGTGCATGG TTGGCATGGC AAAACCGGGC  780
TGAACATTGG CAGCGGGAAC CGCAGCACCT GTTCCGGCCG GCATCACACC GGTAACGCCA  840
TGACCGGCCT GCGCACGGGC CATACTGGCG GTGTAGTCCA TGATCAAGTC ATGTGCCTCG  900
ATCACCGGAG ACCACTGCTG CCGTGCGTCC TGTTGTTGCA CTGCTTCCGG TGCGGTCTGA  960
GTCTGCTGAA ATTGCTGTGT TGCTGTATTC ATACTCCCGA GAGTACGGAT CGAGCAGAAG 1020
CCTGACCATC AGGCTGCGGT ATGAACCTTT TCAACCGCCC CACCCACCTC TCATCCGCAA 1080
GGATTAGAGA TTCGCAGTCG ATGCGACAAT ACTTTTATCA ATGGCAATGT GGATAACTTC 1140
GGAAACTGGC T
```

METHOD FOR CONSTRUCTING NOVEL BACTERIUM BELONGING TO THE GENUS *BIFIDOBACTERIUM*

TECHNICAL FIELD

The present invention relates to a method for producing novel bacteria belonging to the genus *Bifidobacterium*, novel bacteria belonging to the genus *Bifidobacterium* obtained by the method, and a method for detecting the bacteria.

BACKGROUND ART

Bacteria belonging to the genus *Bifidobacterium* are major bacteria in the human intestinal bacterial flora and are known to have beneficial effects on human health, such as regulation of intestinal function, for example, improvement of constipation and diarrhea, suppression of an increase in serum cholesterol, and immunostimulation. For this, a number of commercial products containing the bacteria belonging to the genus *Bifidobacterium* are available in the forms of various fermented foods and drinks, probiotic preparations, and the like. Particularly, fermented milk foods and drinks have excellent palatability; therefore, they are suitable for continuous ingestion of the bacteria belonging to the genus *Bifidobacterium*.

The bacteria belonging to the genus *Bifidobacterium* are obligate anaerobes and susceptible to oxygen, low pH, and high acidity. Thus, there are many difficulties in handling the bacteria belonging to the genus *Bifidobacterium* in fermented milk foods and drinks in terms of proliferation during production, viability during storage, and the like. In order to obtain the physiological effect of the bacteria belonging to the genus *Bifidobacterium*, it is considered necessary to deliver the bacteria alive to the intestine as many as possible. Particularly, increasing the viability of the bacteria in foods and drinks, namely the rate of arrival of ingested bacteria at the intestine, is regarded as an important factor.

In order to solve the above problems, an attempt has been made to improve the viability in fermented milk foods and drinks by improving the production method and adding various viability-improving agents such as N-acetyl glucosamine, pantothenic acid, peptides, and lactulose. However, such a viability-improving agent for the bacteria belonging to the genus *Bifidobacterium* cannot be easily added because not only it increases the production cost but also it causes problems such as reduced palatability. Further, a method that completely blocking the bacteria belonging to the genus *Bifidobacterium* from contacting oxygen by filling a fermented product containing the bacteria into a container composed of an oxygen-impermeable packaging material immediately after the product is produced is also studied. However, no perfect oxygen-impermeable container has yet been available. Further, there is not a lot of flexibility in shaping such a container, and waste disposal is complicated since the container is made by using composite materials. Furthermore, the container itself is expensive, etc. As mentioned above, there are many limitations in using the container.

Accordingly, a fundamental solution for improving the viability of the bacteria belonging to the genus *Bifidobacterium* in fermented foods and drinks is to produce bacteria belonging to the genus *Bifidobacterium* having high viability even under aerobic conditions and under conditions of low pH and high acidity. Examples of such a bacterial strain include *Bifidobacterium breve* YIT 10001 (FERM BP-8205) (Patent Document 1), *Bifidobacterium breve* SBR 3212 (FERM P-11915) (Patent Document 2), and *Bifidobacterium bifidum* YIT 4002 (FERM BP-1038) (Patent Document 3).

However, there has been a problem such that these strains with improved viability are expected to exhibit their effects of improved viability only under conditions in which they are produced. That is, in the production of a mutant strain of the bacteria belonging to the genus *Bifidobacterium*, a method of subculturing and storing bacteria belonging to the genus *Bifidobacterium* in an environment which is harsh for the bacteria to grow and obtaining a surviving strain is normally practiced. While a certain level of viability-improving effect can be expected in an environment under which the mutant strain has been produced, no viability-improving effect can be expected in other environments. Accordingly, the bacteria belonging to the genus *Bifidobacterium* obtained by a conventional method cannot be applied to foods and drinks which are distributed under a condition different from that under which the mutant strain is produced. Accordingly, utility of the conventional method has been extremely limited.

Also, although the cause is unknown, it is known that even a bacterial strain with improved viability obtained by subculturing and storing under conditions with deteriorated environmental factors (for example, a pH in the acidic region) does not exhibit its viability-improvement effect when used under mild conditions at a pH in the neutral region. This has been also one of the reasons for failing to obtain a highly-versatile bacterial strain which is applicable to various foods and drinks.

RELATED ART DOCUMENT

Patent Document

[Patent Document 1] International Publication No. WO03/040350
[Patent Document 2] JP-2922013
[Patent Document 3] JP-B-61-19220

DISCLOSURE OF THE INVENTION

Problem to be Solved by the Invention

Accordingly, an object of the present invention is to provide a method for producing bacteria belonging to the genus *Bifidobacterium* having excellent viability even under various conditions with different environmental factors, novel bacteria belonging to the genus *Bifidobacterium* obtained by the method, and a method for detecting the bacteria.

Means for Solving the Problem

The present inventors conducted an intensive research in order to solve the aforementioned problems. As a result, they have found that, by subculturing and storing bacteria belonging to the genus *Bifidobacterium* alternately in at least two kinds of systems of which conditions are different in environmental factors at least twice, bacteria belonging to the genus *Bifidobacterium* having excellent viability under all the conditions for the alternate subculturing and storing can be obtained.

Furthermore, as a result of a research on a method for specifically detecting the novel bacteria belonging to the genus *Bifidobacterium* thus obtained, they have found a primer capable of specifically amplifying a DNA fragment of the bacteria, and found that the bacteria can be specifically detected and quantified by using the primer. The present inventors have further found that the viable bacterial count of the above bacteria can be quantified with a combination of the primer and a membrane-permeable dye.

That is, the present invention provides a method for producing bacteria belonging to the genus *Bifidobacterium* including subculturing and storing bacteria belonging to the genus *Bifidobacterium* alternately in at least two kinds of systems under conditions with different environmental factors at least twice.

Also, the present invention provides the bacteria belonging to the genus *Bifidobacterium* obtained by the aforementioned method.

Also, the present invention provides a food or drink, particularly a fermented milk food or drink containing the bacteria belonging to the genus *Bifidobacterium*.

Also, the present invention provides a DNA fragment having a nucleotide sequence represented by SEQ ID NO: 1 or SEQ ID NO: 2 or a nucleotide sequence complimentary to the above sequence.

Also, the present invention provides a primer for *Bifidobacterium breve* YIT 12272 (FERM BP-11320) having a nucleotide sequence represented by SEQ ID NO: 1 or SEQ ID NO: 2 or a nucleotide sequence complimentary to the sequence.

Also, the present invention provides a method for detecting *Bifidobacterium breve* YIT 12272 including using the primer.

Also, the present invention provides a method for quantifying a bacterial count of *Bifidobacterium breve* YIT 12272 including using the primer.

Also, the present invention provides a method for quantifying a viable bacterial count of *Bifidobacterium breve* YIT 12272 (FERM BP-11320) including performing a PCR reaction on a sample treated with a membrane-permeable dye by using the primer.

Effect of the Invention

According to the method for producing bacteria belonging to the genus *Bifidobacterium* of the present invention, bacteria belonging to the genus *Bifidobacterium* having excellent viability even in finished products or under conditions different in environmental factors such as distribution conditions can be obtained. Since such a bacterial strain is applicable to various foods and drinks and has high viability in foods and drinks, it can effectively exhibit the physiological effect of the bacteria belonging to the genus *Bifidobacterium*. Also, a bacterial strain utilizable in various foods and drinks can be produced by improving bacteria belonging to the genus *Bifidobacterium* having a specific physiological effect such as an anti-*Helicobacter pylori* bacteria action through the production method of the present invention. For these reasons, the present invention has extremely high industrial applicability.

*Bifidobacterium breve* YIT 12272 having excellent viability can be specifically detected and quantified in foods, drinks, feces, and the intestine by using the DNA fragment of the present invention.

BRIEF DESCRIPTION OF THE DRAWINGS

FIG. 1 shows the nucleotide sequence of the RAPD band specific for *Bifidobacterium breve* YIT 12272. The sequence of a YIT 12272-specific primer is surrounded by a box;

MODES FOR CARRYING OUT THE INVENTION

Figure 2:
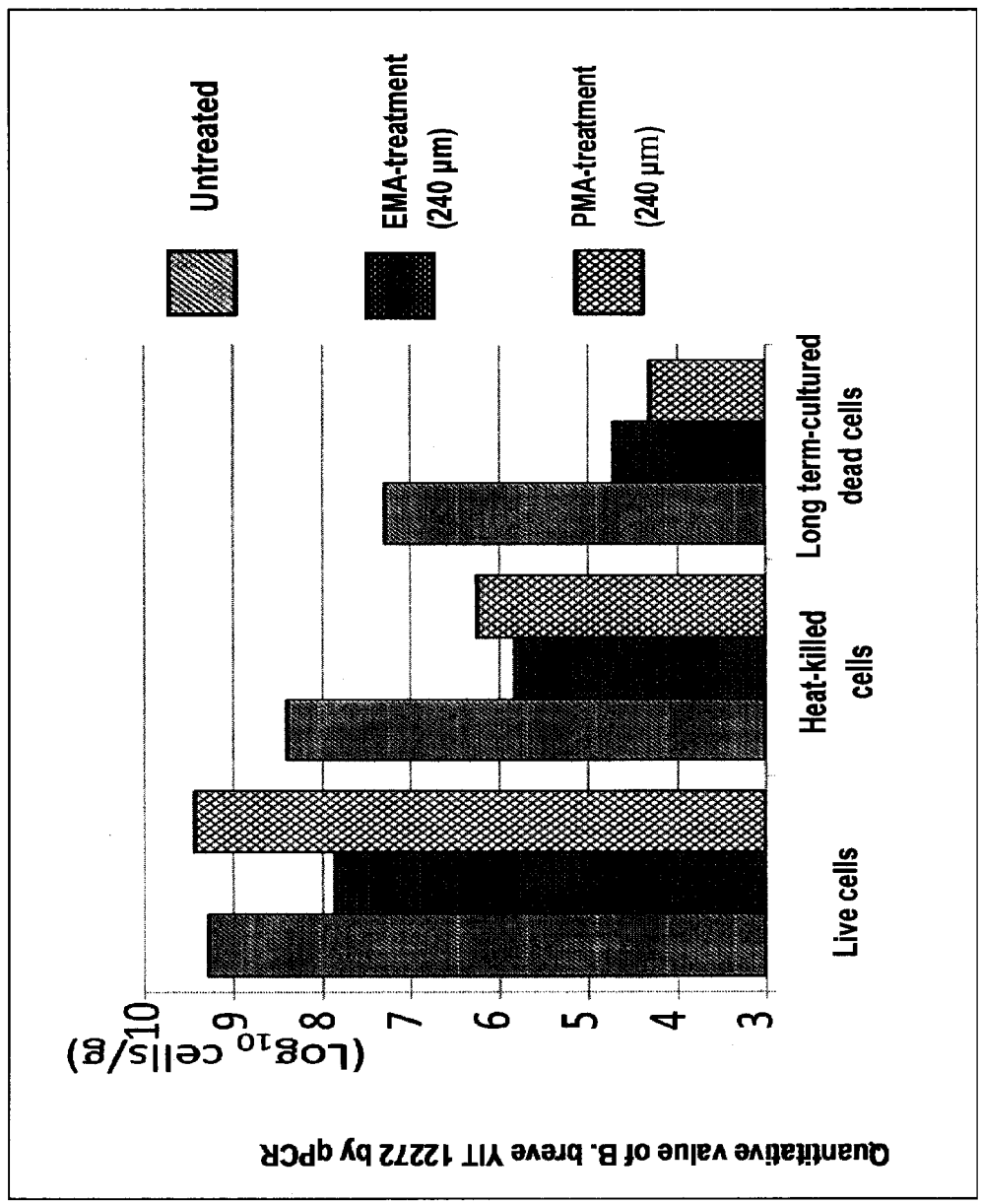
FIG. 2 shows the shift in the quantitative value of YIT 12272 by quantitative PCR with membrane-permeable dye treatment.

In the present invention, an environmental factor refers to any factor which affects the proliferation and viability of the bacteria belonging to the genus *Bifidobacterium*. Examples thereof include pH, osmotic pressure, acidity, culture/storage temperature, culture/storage time, the amount of dissolved oxygen, light, pressure, water activity, a co-existing microorganism, a nutritional factor (for example, sugars, protein, peptide, fats such as a milk fat, vitamins, minerals, a nonfat milk solid, and a growth factor of the bacteria belonging to the genus *Bifidobacterium* such as a yeast extract), an antibiotic, a culture method (such as static culture, stirred culture, shaking culture, and aeration culture), a sterilization method, a blending method, a packing method, and a material of a storage container of a culture broth or a food or drink. Particularly, pH, osmotic pressure, acidity, culture temperature, and a nutritional factor, which are important environmental factors affecting the proliferation and viability of the bacteria belonging to the genus *Bifidobacterium*, are preferably used. Herein, light includes both visible light and non-visible light, and acidity indicates the amount of a 1/10 N aqueous solution of sodium hydroxide (mL) necessary to neutralize 9 g of a sample.

Also, "at least two kinds of systems under conditions with different environmental factors" refer to at least two kinds of systems in which the quality and/or the quantity of certain environmental factors are varied, for example, at least two kinds of systems resulting from varying pH, osmotic pressure, acidity, culture temperature, a nutritional factor, and the like of a culture broth or a food or drink. More specific examples include systems resulting from varying a culture broth or a food or drink by means of changing the pH, for example, from 5 to 3, changing the osmotic pressure, for example, from 600 mOsm (milliosmol) to 950 mOsm, changing the acidity, for example, from 6 to 20, changing the culture temperature of culture broth, for example, from 37° C. to 30° C., changing the sugars in culture broth or food or drink, for example, from digestible sugar to nondigestible sugar, and, for example, increasing the concentration of dissolved oxygen by stirring.

No particular limitation is imposed on either the target environmental factor or the changes in the quality and/or the quantity thereof. However, it is preferable to take into consideration one or more conditions and environmental factors of culture broths or foods and drinks to which the bacteria belonging to the genus *Bifidobacterium* to be produced by the production method of the present invention are applied, select the condition and the environmental factor affecting the proliferation and viability of the bacteria belonging to the genus *Bifidobacterium*, and conduct alternately subculturing and storing of the bacteria under thus selected condition and environmental factor. Although culture conditions of the bacteria belonging to the genus *Bifidobacterium* vary depending on the bacterial species, in general, culture is carried out approximately under the following conditions; a nonfat milk solid content of 5 to 30%, a milk fat content of 0 to 10%, an osmotic pressure of 150 to 1000 mOsm, a pH of 4.0 to 7.0, a concentration of dissolved oxygen of 0 to 2 ppm, and a culture temperature of 30 to 39° C. The conditions can be varied within the above range, or conditions can be set outside the above range. Further, storage conditions vary depending on the kind and the form of a culture broth or a food or drink, for example, the storage temperature for foods and drinks may be a normal temperature, a refrigerated temperature, or a freezing temperature. Thus, the environmental factor and the condition of a culture broth or a food or drink to which the bacteria are applied may be appropriately selected and used.

Also, when a syrup (sweetener) is added to a culture broth to provide a food or drink, various kinds of sugars will be used. In that case, the osmotic pressure may be increased or decreased depending on the kind of sugar used; therefore, such a change in the osmotic pressure may be used as the condition to be varied.

Further, when a food or drink is stored in a blending tank for a certain period of time before filed in a container, the drink or food needs to be homogenized by stirring before filled a container. At this time, oxygen in the head space of the blending tank may be taken in and the concentration of dissolved oxygen is increased to the saturation concentration in some cases. Thus, such a change in the concentration of dissolved oxygen may be used as the condition to be varied.

Although no particular limitation is imposed on the kind of the bacteria belonging to the genus *Bifidobacterium* which can be used in the production method of the present invention, examples thereof include *Bifidobacterium breve, B. longum, B. bifidum, B. animalis, B. suis, B. infantis, B. adolescentis, B. catenulatum, B. pseudocatenulatum, B. lactis*, and *B. globosum*. Among them, *Bifidobacterium breve, Bifidobacterium longum*, and *Bifidobacterium bifidum* are preferable as they have been used in a number of milk products for some time and data of the safety and the like have accumulated, and further, those bacteria exhibit also a high viability-improvement effect. Among them, *Bifidobacterium breve* is particularly preferable.

Using the aforementioned bacteria belonging to the genus *Bifidobacterium* as a parent strain, by alternately subculturing and storing the bacteria belonging to the genus *Bifidobacterium* at least twice in at least two kinds of systems under conditions with different environmental factors, the bacteria belonging to the genus *Bifidobacterium* having excellent viability under all the conditions used for the alternate subculturing and storing can be obtained. Specifically, (1) the parent strain bacteria belonging to the genus *Bifidobacterium* is cultured under environmental factor A to thereby obtain a culture broth or a food or drink. The culture broth or the food or drink thus obtained is stored so that a strain exhibiting improved viability under the conditions with the environmental factor A is concentrated or selected. (2) After that, the strain exhibiting improved viability is cultured under environmental factor B to thereby obtain a culture broth or a food or drink. The culture broth or the food or drink thus obtained is stored so that a strain exhibiting improved viability under the conditions with the environmental factor B is concentrated or selected. (3) The above steps are repeated at least twice, whereby the bacteria belonging to the genus *Bifidobacterium* exhibiting excellent viability under the environmental factors A and B can be obtained.

A method of alternately subculturing and storing, when the conditions are varied based on the environmental factors A and B, includes performing the alternate subculturing and storing in any combination and order such as A→B→A→B→A and A→A→B→B→A→A→B→B→A→A→B→B; however, the alternate subculturing and storing is preferably performed at least twice. It is preferably performed 2 to 100 times, more preferably 4 to 100 times, particularly preferably 4 to 50 times.

At least two kinds of the condition variations of the environmental factor may be set. A method of alternately subculturing and storing in which three condition variations, A, B, and C, are set may be carried out in any way, for example, A→B→C→A→B→C→A→B→C and A→A→A→B→B→C→A→B→B→B→C→C→A.

The environmental factor are preferably changed in at least one kind, further, at least two kinds, and particularly at least three kinds selected from pH, osmotic pressure, acidity, culture temperature, and a nutritional factor in terms of A and B. Herein, these factors are preferably changed in the following range; pH changed by 0.1 to 3 between 4.0 and 7.0, the osmotic pressure changed by 10 to 700 mOsm between 150 and 1000 mOsm, the acidity changed by 1 to 20 between 5 and 30, and the culture temperature changed by 1 to 6° C. between 30 and 39° C. As the nutritional factor, it is preferable to change the kind of sugar from palatinose to reduced maltose syrup. Also, a milk fat content is preferably changed by 0.1 to 6% between 0 and 10%. Also, a nonfat milk solid content is preferably changed by 0.1 to 20% between 5 and 30%.

Further, it is also possible to treat the parent strain of bacteria belonging to the genus *Bifidobacterium* with a mutation-inducing agent and the like such as ultraviolet rays, nitrosoguanidine (NTG), and ethyl methanesulfonate (EMS), and subject the mutation-inducing agent-treated parent strain to the aforementioned alternate subculturing and storing to select a bacterial strain having desired quality.

Herein, the viability indicates approximately how many live bacteria are present in a culture broth or a food or drink after storage, and the viable bacterial count can be obtained by an ordinary method. For example, a culture broth, or a drink or food used for storage is appropriately diluted and applied to a TOS propionate agar medium, followed by anaerobic culture at 37° C. for 72 hours. Then, the viable bacterial count can be obtained by determining colonies formed on the medium. The viability can be indicated based on the proportion of the viable bacterial count in a culture broth, or a drink or food used for storage after storage to that before storage.

Any medium in which the bacteria belonging to the genus *Bifidobacterium* can grow, such as a GAM medium, a MILS medium (Iwata & Morishita, Letter in Applied Microbiology, vol. 9, 165-168, 1989), a TOS propionate medium, soybean milk, vegetable juice, fruit juice, and wort can be used as a culture broth in the production method of the present invention. However, a medium containing milk as a main component is preferable, and examples of the milk include cow milk (whole milk) and a processed product thereof such as defatted milk and a milk-derived peptide. A nonfat milk solid content and a fat content can be set at any amount depending on the milk material to be used and the blending amount thereof, and a growth factor of the bacteria belonging to the genus *Bifidobacterium* such as a yeast extract may be added. Any of these nonfat milk solid content, fat content, and growth factor of the bacteria belonging to the genus *Bifidobacterium* can be an environmental factor.

Also, the environmental factor of fermented milk foods and drinks obtained by adding an optional ingredient such as a syrup to a culture broth containing a milk medium is close to that of a finished product; therefore, bacteria exhibiting high viability in a finished product can be more efficiently concentrated. Thus, the fermented milk foods and drinks are preferably used for the aforementioned breeding and improvement of the bacterial strain. An optional ingredient, for example, a syrup (sweetener) such as sugars, an emulsifying agent, a thickener (a stabilizer), vitamins, and minerals can be added to the fermented milk foods and drinks, any of which can be an environmental factor. Examples of the syrup include sugars such as glucose, sucrose, fructose, high-fructose corn syrup, glucose fructose syrup, palatinose, trehalose, lactose, xylose, malt sugar, honey, and molasses, sugar alcohol such as sorbitol, xylitol, erythritol, lactitol, palatinit, a reduced sugar syrup, and a reduced malt sugar syrup, a highly-sweet sweetener such as aspartame, thaumatin, sucralose, acesulfame-K, and stevia. Also, an emulsifying agent such as a sucrose fatty acid ester, a glycerin fatty acids ester, a polyglycerin fatty acid ester, a sorbitan fatty acid ester, and lecithin, a thickener (a stabilizer) such as agar, gelatin, carrageenan, guar gum, xanthan gum, pectin, locust bean gum, gellan gum, carboxymethyl cellulose, soybean polysaccharide, and propylene glycol alginate may be added to the fermented milk foods and drinks. Besides these, vitamins such as vitamin A, vitamin Bs, vitamin C, vitamin D, and vitamin Es, minerals such as calcium, magnesium, zinc, iron, and manganese, an acidifier such as citric acid, lactic acid, acetic acid, malic acid, tartaric acid, and gluconic acid, a milk fat content such as cream, butter, and sour cream, flavors of, for example, yoghurt, berry, orange, Chinese quince, perilla, citrus, apple, mint, grape, apricot, pear, custard cream, peach, melon, banana, the tropics, herb, tea, and coffee, a herb extract, and a brown sugar extract, and the like can be added.

For the culture broth and the fermented milk food or drink, microorganisms other than the bacteria belonging to the genus *Bifidobacterium* can also be used in combination. Examples of the microorganism include bacteria belonging to the genus *Lactobacillus* such as *Lactobacillus casei, L. acidophilus, L. plantarum, L. buchneri, L. gallinarum, L. amylovorus, L. brevis, L. rhamnosus, L. kefiri, L. paracasei, L. curvatus, L. zeae, L. helveticus, L. salivarius, L. gasseri, L. fermentum, L. reuteri, L. crispatus, L. delbrueckii* subsp. *bulgaricus, L. delbrueckii* subsp. *delbrueckii*, and *L. johnsonii*, bacteria belonging to the genus *Streptococcus* such as *Streptococcus thermophilus*, bacteria belonging to the genus *Lactococcus* such as *Lactococcus lactis* subsp. *lactis* and *Lactococcus lactis* subsp. *cremoris*, bacteria belonging to the genus *Enterococcus* such as *Enterococcus faecalis* and *E. faecium*, bacteria belonging to the genus *Bacillus* such as *Bacillus subtilis*, yeast belonging to the genus *Saccharomyses, Torulaspora*, and *Candida* such as *Saccharomyces cerevisiae, Torulaspora delbrueckii*, and *Candida kefyr*.

The fermented foods and drinks can be produced according to an ordinary method. For example, when producing fermented milk foods and drinks, the parent strain of bacteria belonging to the genus *Bifidobacterium* is inoculated into a sterilized milk medium alone or in combination with other microorganisms and cultured, and the resulting product is subjected to homogenization treatment to give fermented milk. Subsequently, a separately-prepared syrup solution is added and mixed, and the resulting product is homogenized using a homogenizer and the like, and a flavor is further added to prepare the final product.

By the aforementioned method, using *Bifidobacterium breve* YIT 4125 (FERM BP-7813) as the parent strain, one strain of the bacteria belonging to the genus *Bifidobacterium* exhibiting particularly excellent viability under the conditions of different environmental factors was produced. The bacterial strain thus obtained was deposited as *Bifidobacterium breve* YIT 12272 (deposited under the terms of the Budapest Treaty under accession number FERM BP-11320) at International Patent Organism Depositary, National Institute of Advanced Industrial Science and Technology (Tsukuba Central 6, 1-1-1 Higashi, Tsukuba, Ibaraki) on Feb. 16, 2010. *Bifidobacterium breve* YIT 12272 has the following bacteriological characteristics in comparison with its parent strain, *Bifidobacterium breve* YIT 4125.

TABLE 1

Bacterial cell morphology and characteristics of the colony

| | YIT 4125 Strain | YIT 12272 Strain |
|---|---|---|
| Gram stain | Positive | Positive |
| Morphology of bacterial cell | Pleomorphic *bacillus* | Pleomorphic *bacillus* |
| Colony color | White | White |
| Colony form | Circle with smooth margin | Circle with smooth margin |

Bacterial cells of each strain were cultured on an agar-added MILS medium (Iwata & Morishita, Letter in Applied Microbiology, vol. 9, 165-168, 1989) at 37° C. under anaerobic condition (Anaero Pack (Mitsubishi gas chemical company, Inc.)) and a single colony was picked up from the agar medium (single colony isolation). This process of single colony isolation was repeated to purify a bacterial strain. Then, the bacterial morphology (culturing in the MILS medium overnight, followed by gram stain) and the characteristic of the colony (culturing on the agar medium) of the purified bacterial strain were observed.

TABLE 2

Results of sugar fermentation character test by API 50CH

| | YIT 4125 | YIT 12272 |
|---|---|---|
| Control | − | − |
| Glycerol | − | − |
| Erythritol | − | − |
| D-Arabinose | ± | − |
| L-Arabinose | − | − |
| D-Ribose | + | + |
| D-Xylose | − | − |
| L-Xylose | − | − |
| D-Adonitol | − | − |
| Methyl-βD-Xylopyranoside | − | − |
| D-Galactose | + | + |
| D-Glucose | + | + |
| D-Fructose | + | + |
| D-Mannose | (+) | + |
| L-Sorbose | − | − |
| L-Rhamnose | − | − |
| Dulcitol | − | − |
| Inositol | − | − |
| D-Mannitol | − | − |
| D-Sorbitol | − | − |
| Methyl-αD-Mannopyranoside | − | − |
| Methyl-αD-Glucopyranoside | + | + |
| N-Acetyl-Glucosamine | − | − |
| Amygdalin | + | + |
| Arbutin | + | + |
| Esculinferric citrate | + | + |
| Salicin | + | + |
| D-Cellobiose | + | + |
| D-Maltose | + | + |
| D-Lactose | + | + |
| D-Melibiose | + | + |
| D-Sucrose | + | + |
| D-Trehalose | ± | (+) |
| Inulin | − | − |
| D-Melezitose | + | + |
| D-Rafinose | + | + |
| Starch | − | (+) |
| Glycogen | − | − |
| Xylitol | − | − |
| Gentiobiose | + | + |
| D-Turanose | + | + |
| D-Lyxose | ± | − |
| D-tagatose | − | − |

TABLE 2-continued

Results of sugar fermentation character test by API 50CH

|  | YIT 4125 | YIT 12272 |
|---|---|---|
| D-Fucose | − | − |
| L-Fucose | (+) | (+) |
| D-Arabitol | − | − |
| L-Arabitol | − | − |
| Gluconate | − | − |
| 2 Keto Gluconate | − | − |
| 5 Keto Gluconate | − | − |

+: Strongly positive
(+): Weakly positive
−: Negative
±: Negative or delayed weakly positive In accordance with the manual of API 50CH (the product of bioMerieux Japan), each bacterial suspension after overnight culture was inoculated into the medium containing each substrate and then anaerobically cultured at 37° C. for seven days. After that, the fermentation characteristic for each substrate was determined.

No particular limitation is imposed on the utilization form of the bacteria belonging to the genus *Bifidobacterium* obtained by the method of the present invention, and lyophilized bacteria may be used or a culture product containing the bacteria may also be used. However, in any form, the bacteria are preferably alive.

The bacteria belonging to the genus *Bifidobacterium* obtained by the method of the present invention may be mixed with a solid or liquid pharmaceutical nontoxic carrier and used in the form of a conventional pharmaceutical preparation. Examples of the preparation include a solid preparation such as a tablet, a granule, powder, and a capsule, a liquid preparation such as a solution, a suspension, and an emulsion, and a lyophilized preparation. These preparations may be prepared by an ordinary method used in the pharmaceutical preparation technology. Examples of the pharmaceutical nontoxic carrier includes glucose, lactose, sucrose, starch, mannitol, dextrin, fatty acid glyceride, polyethylene glycol, hydroxyethyl starch, ethylene glycol, polyoxyethylene sorbitan fatty acid esters, amino acid, gelatin, albumin, water, and physiological saline. Also, a conventional additive such as a stabilizer, a humectant, an emulsifying agent, a binder, a tonicity adjusting agent, and a dilluent can be appropriately added as needed.

The bacteria belonging to the genus *Bifidobacterium* obtained by the method of the present invention can be not only prepared as a pharmaceutical preparation as described above but also used by adding to foods and drinks. When added to foods and drinks, the bacteria may be added alone or together with various nutritional ingredients. Specifically, when adding the bacteria belonging to the genus *Bifidobacterium* obtained by the method of the present invention to foods and drinks, an additive which is utilizable in foods and drinks can be appropriately used, and the foods and drinks may be shaped into a form suitable for consumption, specifically a granule, a grain, a tablet, a capsule, a paste, and the like by conventional means. Further, the bacteria may be added to various food products, for example, a processed meat product such as ham and sausage, a processed seafood product such as cooked minced fish (kamaboko) or fish sausage (chikuwa), bread, confectionary, butter, and dry milk, or the bacteria may also be added to drinks such as water, fruit juice, milk, a soft drink, and a tea drink. It is to be noted that the foods and drinks also include feed for the animal.

The bacteria belonging to the genus *Bifidobacterium* obtained by the method of the present invention can be applied to various kinds of foods and drinks of different environments, and owing to its high viability in foods and drinks, the bacteria belonging to the genus *Bifidobacterium* can effectively exhibit their general physiological function such as an intestine-regulating action. Also, improving the bacteria belonging to the genus *Bifidobacterium* naturally having a specific physiological effect such as a *Helicobacter pylori* bacteria-eradication action by the production method of the present invention enables utilization of the bacterial strain in various foods and drinks. This increases the palatability of the foods and drinks containing the bacterial strain, and at the same time broadens consumers' choice. Further, improving the viability of the bacterial strain can enhance the physiological effect of the bacterial strain.

Further, the food and drink are preferably used as fermented foods and drinks such as fermented milk foods and drinks, fermented soymilk, fermented fruit juice, and fermented vegetable juice containing live bacteria belonging to the genus *Bifidobacterium* obtained by the method of the present invention. Among them, fermented milk foods and drinks are preferably employed. These fermented milk foods and drinks may be produced by an ordinary method, and can be produced by the aforementioned method. The fermented milk foods and drinks thus obtained may also be provided as a product in the form of any of a plain type without syrup (a sweetener), a soft type, a fruit-flavored type, solid, liquid, and the like.

Further, the present invention relates to foods and drinks containing the bacteria belonging to the genus *Bifidobacterium* obtained by the method of the present invention, particularly fermented milk foods and drinks containing a sweetener. The kind, the production method, and the form of the fermented milk foods and drinks may be similar to those described above. It is preferable to produce fermented milk foods and drinks using a combination of the bacteria belonging to the genus *Bifidobacterium* obtained by the method of the present invention and at least one kind of bacterium selected from bacteria belonging to the genus *Lactobacillus*, bacteria belonging to the genus *Streptococcus*, and bacteria belonging to the genus *Lactococcus* because high palatability is attained, and this enables continuous ingestion.

Further, for foods and drinks prepared by using the bacteria belonging to the genus *Bifidobacterium*, a container composed of an oxygen-impermeable packaging material such as glass and aluminum-coated paper has been mainly used for the purpose of increasing the viability of the bacteria during storage. However, because the bacteria belonging to the genus *Bifidobacterium* obtained by the method of the present invention do not require a strict anaerobic condition owing to its high viability, highly oxygen-permeable resin (such as polystyrene, polyethylene, and polyethylene terephthalate) can also be used as a material for the container. A container made of such a resin has merits of low cost and high flexibility in forming, as compared with a container composed of an oxygen-impermeable packaging material.

A DNA fragment and a primer of the present invention have a nucleotide sequence represented by SEQ ID NO: 1 or SEQ ID NO: 2 or a nucleotide sequence complimentary to the sequence. The DNA fragment primer of the present invention can be obtained by performing PCR on DNA derived from numerous bacteria belonging to the genus *Bifidobacterium* and related bacteria and searching through RAPD method. That is, PCR is performed on DNA derived from bacteria belonging to the genus *Bifidobacterium* using numerous random primers to amplify a DNA fragment sandwiched between the random primers. Based on the RAPD band pattern thus obtained, cloning is performed and the nucleotide sequence of the *Bifidobacterium breve* YIT 12272-specific PCR amplification product is determined (SEQ ID NO: 3). The DNA fragment primer of the present invention is designed based on the nucleotide sequence thus determined (SEQ ID NOs: 1 and 2). The DNA fragment primer of the present invention includes a DNA fragment primer having a nucleotide sequence complementary to the nucleotide sequence represented by SEQ ID NO: 1 or 2.

For the primer of the present invention, a combination of two nucleotide sequences represented by SEQ ID NOs: 1 and 2; or a combination of two nucleotide sequences complementary to the sequences is more preferably used. Furthermore, it is preferable to use a primer having a sequence of SEQ ID NO: 1 or a sequence complementary to the sequence as a forward primer and a primer having a sequence of SEQ ID NO: 2 or a sequence complementary to the sequence as a reverse primer.

The primer of the present invention is specific for the *Bifidobacterium breve* YIT 12272, and useful for detection, quantification of the bacterial count, and quantification of the viable bacterial count for the *Bifidobacterium breve* YIT 12272. Examples of a sample for the detection and quantification method of the present invention include foods and drinks, pharmaceutical products, and feces containing YIT 12272.

Examples of the method of detecting and quantifying YIT 12272 include the steps of (1) extracting DNA from a sample, (2) performing a PCR reaction using the primer of the present invention, and (3) detecting the DNA fragment amplified by the step (2).

In more detail, first, DNA is extracted from feces, foods, drinks, and the like, as a sample for PCR. As a method of extracting DNA from a diluted solution of feces and the like, Marmur's method which is the standard method, an enzyme method which is the modified Marmur's method, and a benzyl chloride method are preferable. Further, a sample obtained by suspending some of the bacterial cells in a buffer or sterilized water, followed by heating at 95° C. for approximately 15 minutes can be provided as a template for PCR.

A target DNA fragment (PCR product) can be obtained by carrying out the amplification reaction using a combination of DNA thus extracted and the primer of the present invention. Generally, when using a primer in PCR method and the like, it is preferable to use a pair of two kinds of primers. For example, by using a primer set of primers having nucleotide sequences of SEQ ID NOs: 1 and 2, only a region sandwiched between the primers in DNA of the *Bifidobacterium breve* YIT 12272 can be amplified among other numerous kinds of bacteria which are present, whereby the bacteria can be identified. Also, when performing PCR, quantification of the target bacteria is also possible by subjecting template DNA to serial dilution in advance to find the detection limit and then the similar analysis is conducted.

The DNA thus obtained may be subjected to electrophoresis, and the *Bifidobacterium breve* YIT 12272 can be identified based on the presence or absence of a band.

Also, only live bacteria of the *Bifidobacterium breve* YIT 12272 can be detected and quantified by performing PCR reaction on a sample after treated with a membrane-permeable dye. Examples of a membrane-permeable dye to be used include ethidium monoazide (EMA) and propidium monoazide (PMA), and propidium monoazide (PMA) is particularly preferable. The membrane-permeable dye treatment of a sample is carried out by, for example, adding a membrane-permeable dye solution having a final concentration of 5 to 250 µM, followed by irradiation of light. PCR reaction may be performed in a same manner as mentioned above.

EXAMPLES

Hereinbelow, the content of the present invention will be described further in detail with Examples; however, the present invention is not limited in any way by these Examples.

Example 1

Breeding and Improving *Bifidobacterium breve* YIT 10001 and YIT 4125 by the Alternate Subculture Method Using *Bifidobacterium breve* YIT 10001 strain (FERM BP-8205) and *Bifidobacterium breve* YIT 4125 strain (FERM BP-7813) as the parent strain, the alternate subculturing and concentrating of the bacteria is conducted.

(1) After sterilizing 20.7% whole milk powder medium at 135° C. for 3.5 seconds, 0.5% of seed starter 1 of *Bifidobacterium breve* YIT 10001 strain or YIT 4125 strain and 1% of a seed starter of *Bifidobacterium bifidum* were inoculated and then cocultured at 33° C. until the pH reached 5.3, whereby bacterial suspension A1 (400 mL) was prepared.

(2) Into the bacterial suspension A1, syrup solution A was blended to 10% of the final concentration of palatinose, whereby milk product A1 (630 mL) was prepared. The milk product A1 (200 mL) was dispensed into 300-mL flasks, followed by storage at 5° C. for one week while stirring (90 rpm) under aerobic conditions with a cotton plug (hereinafter, abbreviated as aerobic stirring storage). Subsequently, test tubes were filled up with the resulting milk product A1 and closed with a butyl stopper, followed by static storage at 10° C. for one week under anaerobic conditions (hereinafter, abbreviated as anaerobic static storage).

(3) The milk product A1 (1 mL) stored under the above conditions was inoculated in 10 mL of a cephalothin-added milk medium (12% defatted milk, 0.1% yeast extract, 0.03% L-cysteine hydrochloride, 0.2% sedimentary calcium carbonate, and 5 µg/mL cephalothin, hereinafter, abbreviated as a cephalothin-added milk medium), followed by anaerobic culture at 37° C. for 24 hours, whereby mother starter 2 of *Bifidobacterium breve* was obtained. The mother starter 2 (0.03 mL) was inoculated in 30 mL of a milk medium (12% defatted milk, 0.1% yeast extract, 0.03% L-cysteine hydrochloride, 0.2% sedimentary calcium carbonate, hereinafter abbreviated as a milk medium), followed by anaerobic culture at 37° C. for 24 hours, whereby seed starter 2 of *Bifidobacterium breve* was prepared. Similar operations as above were repeated using the seed starter 2. That is, milk product A2 prepared by using the seed starter 2 was subjected to aerobic stirring storage, followed by anaerobic static storage, whereby mother starter 3 of *Bifidobacterium breve*, and further, seed starter 3 of *Bifidobacterium breve* were prepared.

(4) Subsequently, a 23.5% defatted milk medium was sterilized at 120° C. for 3.5 seconds, and 2% of the seed starter 3 of *Bifidobacterium breve* and 0.01% of a seed starter of *Lactococcus* lactis were inoculated and then mixed and cocultured at 37° C. until the pH reached 4.4, whereby bacterial suspension B1 (100 mL) was prepared.

(5) Further, to a 19.7% defatted milk medium which was sterilized at 120° C. for 3.5 seconds, 0.08% of milk peptide was added, and then 0.5% of a seed starter of *Streptococcus thermophilus* was inoculated and cultured at 37° C. until the pH reached 4.3, whereby bacterial suspension C1 (700 mL) was prepared. The bacterial suspension C1 was added to bacterial suspension B1 (blending ratio 1:2), and further, syrup solution B was blended to 5% of the final concentration of reduced maltose syrup, whereby milk product B1 (870 mL) was prepared.

(6) Similarly to the milk product A1, the milk product B1 (1 mL) was subjected to aerobic stirring storage, followed by anaerobic static storage, and then inoculated in 10 mL of the cephalothin-added milk medium, followed by anaerobic culture at 37° C. for 24 hours to provide mother starter 4 of *Bifidobacterium breve*. The mother starter 4 (0.03 mL) was inoculated in 30 mL of the milk medium, followed by anaerobic culture at 37° C. for 24 hours, whereby seed starter 4 of *Bifidobacterium breve* was prepared. Similar operations as above were repeated using the seed starter 4. That is, milk product B2 prepared with the seed starter 4 was subjected to aerobic stirring storage, followed by anaerobic static storage, whereby mother starter 5, and further, seed starter 5 of *Bifidobacterium breve* were prepared.

As shown above, preparation, aerobic stirring storage, and anaerobic static storage of the milk product A were repeated twice. Subsequently, using surviving *Bifidobacterium breve*, preparation, aerobic stirring storage, and anaerobic static storage of the milk product B were repeated twice and the *Bifidobacterium breve* was concentrated. A series of the above steps was set as one cycle, which was repeated for a total of four cycles. Finally, milk product A8 and milk product B8 were subjected to anaerobic static storage at 10° C. for two weeks and then a portion (1 mL) of each products was applied to a TOS propionate agar medium (Yakult Pharmaceutical Industry Co., Ltd.) containing 5 μg/mL cephalothin and anaerobic culture was conducted at 37° C. by using Anaero Pack (Mitsubishi gas chemical company, Inc.) to isolate single colony. The single colony isolation was repeated for purification, whereby single colonies of a total 42 strains derived from *Bifidobacterium breve* YIT 10001 strain and YIT 4125 strain, specifically a total of 21 strains from milk product A8 and a total of 21 strains from milk product B8, were isolated.

Example 2

Viability Confirmatory Assay

Using the parent strain and the isolated strains, milk products A and B were each prepared and stored while stirring at 5° C. for one week under aerobic conditions, followed by static storage at 10° C. for two weeks under anaerobic conditions in accordance with the method of Example 1. Then, *Bifidobacterium breve* YIT 12272 strain (derived from YIT 4125 strain, isolated from the milk product A8), which exhibited excellent viability in both of the milk products A and B, was selected.

The results of viability of YIT 12272 strain and control strain (YIT 10001 strain and YIT 4125 strain) in the milk products A and B are shown in Table 3. With respect to YIT 12272 strain, $3\times10^7$ CFU/mL or more live cell survived after storage while stirring at 5° C. for one week under aerobic conditions, followed by static storage at 10° C. for two weeks under anaerobic conditions in both of the milk products A and B. In contrast, in milk products A and B prepared by using each control bacteria, $3\times10^7$ CFU/mL or more live cells survived in one of the milk products; however, the control bacteria did not exhibit excellent viability in both of the products.

Also, the physical properties of the milk product A and B are shown in Table 4. Syrup A was blended into bacterial suspension A to prepare milk product A, of which the pH and the acidity were found to be 5.6 and 3.4, respectively. Although the osmotic pressure of the bacterial suspension A was 550 mOsm, it was increased to 950 mOsm in the milk product A. Meanwhile, bacterial suspension C and syrup B were blended into bacterial suspension B to prepare milk product B, of which the pH and the acidity were found to be 4.4 and 7.5, respectively. Although the osmotic pressure of bacterial suspension B was 900 mOsm, it was decreased to 600 mOsm in the milk product B.

As shown above, it was revealed that the viability of *Bifidobacterium breve* YIT 12272 strain was enhanced, compared with the control strain, in both of the milk products A and B, which differed in culture temperature, pH, acidity, a change in the osmotic pressure due to blending of syrup, a nonfat milk solid content, and a milk fat content.

TABLE 3

The viable bacterial count of *Bifidobacterium breve* YIT 12272 strain in milk products A and B after storage

| | Viable bacterial count(CFU/mL) | |
|---|---|---|
| | Milk product A | Milk product B |
| Test strain | | |
| YIT 12272 Strain | $1.2 \times 10^8$ | $5.8 \times 10^7$ |
| Control strain | | |
| YIT 10001 Strain | $6.0 \times 10^6$ | $4.1 \times 10^7$ |
| YIT 4125 Strain | $1.0 \times 10^8$ | $6.0 \times 10^6$ |

The viable bacterial count was determined on a TOS propionate agar medium containing 5 μg/mL cephalothin after storage while stirring at 5° C. for one week under aerobic conditions, followed by static storage under anaerobic condition at 10° C. for two weeks.

TABLE 4

The physical properties of milk products A and B

| | Milk product A | | Milk product B | |
|---|---|---|---|---|
| | Bacterial suspension A | Product | Bacterial suspension B | Product |
| Culture temperature (° C.) | 33 | | 37 | |
| pH | 5.3 | 5.6 | 4.4 | 4.4 |
| Acidity | 6.0 | 3.4 | 20.7 | 7.5 |
| Osmotic pressure (mOsm) | 550 | 950 | 900 | 600 |
| Nonfat milk solid content (%) | 14.5 | 9.4 | 22.4 | 8.9 |
| Milk fat content (%) | 5.2 | 3.4 | 0.2 | 0.1 |

The osmotic pressure was measured with Osmostat OM-6040 manufactured by Kyoto Daiichi Kagaku.

Example 3

Confirmatory Test for Resistance Against Artificial Gastric Juice

*Bifidobacterium breve* YIT 12272 strain and control strain (YIT 10001 strain and YIT 4125 strain) were each anaerobically cultured overnight at 37° C. in the milk medium. Then, 0.5 mL of the bacterial culture thus obtained was added to 10 mL of artificial gastric juice which had been warmed at 37° C. for 30 minutes, immediately mixed, and then incubated at 37° C. At 0 minute and 120 minutes after the incubation (artificial gastric juice treatment), 1 mL of the mixture was collected and appropriately diluted, and after that the viable bacterial count was determined using a TOS propionate agar medium (Yakult Pharmaceutical Industry Co., Ltd., 37° C., anaerobic culture).

The artificial gastric juice was prepared as follows. That is, the following substances were dissolved in ion-exchange water so that the final concentration of each substance was; proteose peptone (Becton, Dickinson and Co.): 5 g/L, gastric mucin (Wako Pure Chemical Industries, Ltd.): 1.5 g/L, sodium chloride: 5 g/L, sodium bicarbonate: 3 g/L, and potassium dihydrogen phosphate: 1 g/L. The pH of the resulting solution was adjusted to 2.8 with 3.6 N hydrochloric acid, and the solution thus obtained was sterilized by autoclaving at 115° C. for 15 minutes, and then stored at 4° C. Subsequently, pepsin (Wako Pure Chemical Industries, Ltd.) was dissolved in ion-exchange water at 400 mg/L, and the resulting solution was sterilized by filtration through a membrane filter (DISMIC-25cs, Advantec, 0.45 μm) to give a pepsin solution. The pH of the solution was re-adjusted to 2.8, and 20 mL of the pepsin solution was added to 180 mL of the solution prepared as above right before use, whereby artificial gastric juice was prepared.

The viable bacterial counts at 0 minute and 120 minutes after the artificial gastric juice treatment are shown in Table 5. Although the viable bacterial count of *Bifidobacterium breve* YIT 12272 strain was hardly changed even 120 minutes after the artificial gastric juice treatment, the viable bacterial count of the control strain (YIT 10001 strain and YIT 4125 strain) was decreased by the treatment. It was revealed that resistance of YIT 12272 strain against artificial gastric juice was also enhanced, compared with the control strain.

TABLE 5

Resistance of *Bifidobacterium breve* YIT 12272 strain against artificial gastric juice

|  | Viable bacterial count (CFU/mL) | |
|---|---|---|
|  | 0 minute after artificial gastric juice treatment | 120 minute after artificial gastric juice treatment |
| Test strain | | |
| YIT 12272 Strain | $2.4 \times 10^8$ | $2.1 \times 10^8$ |
| Control strain | | |
| YIT 10001 Strain | $3.0 \times 10^8$ | $1.7 \times 10^5$ |
| YIT 4125 Strain | $3.9 \times 10^8$ | $3.0 \times 10^7$ |

Example 4

Confirmatory Assay for Resistance Against Sequential Treatment with Artificial Gastric Juice/Artificial Bile and Intestinal Fluid Using *Bifidobacterium breve* YIT 12272 strain and control strain (YIT 10001 strain and YIT 4125 strain), milk product B was prepared similarly to Example 1. The milk products B (200 mL) prepared by using each bacterial strain were each dispensed into 300-mL flasks, followed by storage at 5° C. for one week while stirring (90 rpm) under aerobic conditions with a cotton plug. Subsequently, test tubes were filled up with the resulting milk products B, followed by static storage at 10° C. under anaerobic conditions with a butyl stopper. It is to be noted that only the gas phase of a 300-mL flask containing the milk product B prepared by using YIT 4125 strain was replaced by nitrogen gas, and then the resulting product was stored at 5° C. for one week while stirring (90 rpm) under anaerobic conditions with a butyl stopper, followed by static storage at 10° C. under anaerobic conditions.

Similarly to the method of Example 3, the artificial gastric juice treatment was performed by adding 0.5 mL of the milk product B which had been subjected to static storage at 10° C. for four days to 10 mL of artificial gastric juice adjusted to pH of 3.3, followed by incubation at 37° C. for 60 minutes. To 2 mL of the test solution thus obtained, 1 mL of artificial bile which had been warmed at 37° C. in advance was added, immediately followed by stirring. Subsequently, to the mixture thus obtained, a 5 mL mixture of 4 mL of artificial intestine fluid and 1 mL of artificial pancreatic fluid, which had been warmed at 37° C. for 30 minutes, were added, and the resulting mixture was stirred and incubated at 37° C. Then, at 0 minute and 60 minutes after the artificial gastric juice treatment and 60 minutes after the artificial bile and intestinal fluid treatment, 1 mL of the resulting mixture was collected each time, and appropriately diluted, and the viable bacterial count was determined using a TOS propionate acid agar medium (Yakult Pharmaceutical Industry Co., Ltd., 37° C., anaerobic culture).

The artificial bile was prepared by dissolving bile powder (Oxgall, Difco) in ion-exchange water at 40 g/L and adjusting the pH of the resulting solution to 8.0 with 3 M sodium carbonate, and then diluting the resulting solution with ion-exchange water so that the concentration of the bile powder was 1% (W/V), followed by sterilization by autoclaving at 121° C. for 15 minutes. The artificial bile thus prepared was used. Also, the artificial intestine fluid was prepared by dissolving the following substances in ion-exchange water so that the final concentration of each substance was; sodium chloride: 5 g/L, potassium chloride: 1 g/L, and sodium bicarbonate: 3 g/L, and adjusting the pH of the resulting solution to 8.0 with 3 M sodium carbonate, followed by sterilization by autoclaving at 121° C. for 15 minutes. The artificial pancreatic fluid was prepared by dissolving pancreatic lipase (MP Biomedicals) in the artificial intestine fluid at 20 g/L immediately before the test, and the resulting solution was sterilized by filtration through a membrane filter (DISMIC-25cs, Advantec 0.45 μm), followed by storage on ice. The artificial pancreatic fluid thus prepared was used.

The viable bacterial count at 0 minute and 60 minutes after the artificial gastric juice treatment, and 60 minutes after the artificial bile and intestine fluid treatment are shown in Table 6. The viable bacterial count of *Bifidobacterium breve* YIT 12272 strain in the stored milk product B was higher than that of the control strain (*Bifidobacterium breve* YIT 10001 strain and YIT 4125 strain) not only after the artificial gastric juice treatment but also after the sequential treatment with artificial gastric juice and intestinal fluid containing artificial bile. It was revealed that YIT 12272 strain was more enhanced for both the artificial gastric juice-resistance and the artificial bile/intestinal fluid-resistance than the control bacteria.

TABLE 6

Resistance of *Bifidobacterium breve* YIT 12272 strain in milk product B against the sequential treatment with artificial gastric juice/artificial bile and intestinal fluid after storage

|  | Viable bacterial count (CFU/mL) | | |
|---|---|---|---|
|  | 0 minute after the artificial gastric juice treatment | 60 minute after the artificial gastric juice treatment | 60 minutes after the artificial bile and intestinal fluid treatment |
| Test strain | | | |
| YIT 12272 Strain | $6.9 \times 10^7$ | $2.8 \times 10^6$ | $2.1 \times 10^5$ |
| Control strain | | | |
| YIT 10001 Strain | $4.9 \times 10^7$ | $3.2 \times 10^4$ | $5.3 \times 10^2$ |
| YIT 4125 Strain | $8.1 \times 10^7$ | $2.6 \times 10^5$ | $3.1 \times 10^3$ |

The milk product B was stored while stirring at 5° C. for one week under aerobic conditions (only YIT 4125 strain was stored under anaerobic conditions), followed by storage for four days at 10° C. under anaerobic conditions, and then treated with artificial gastric juice (pH 3.3), and sequentially with artificial bile (1% bile powder). The viable bacterial count was enumerated in the milk product B thus obtained.

Example 5

Production of Fermented Milk Foods and Drinks

Into 506 g of water, 124 g of whole milk powder was dissolved, followed by sterilization at 135° C. for 3 seconds. Subsequently, 0.5% of *Bifidobacterium breve* YIT 12272 strain, 1% of *Bifidobacterium bifidum*, and 0.001% of *Lactobacillus acidophilus* were inoculated and cultured at 33° C. until the pH reached 5.3. The resulting mixture was homogenized at 15 MPa to give 630 g of a bacterial suspension. Meanwhile, 98 g of palatinose, 8 g of carrot juice, 2.5 g of DHA-containing oil, 7 g of emulsified calcium, 0.1 g of lactoferrin, 0.02 g of vitamin D, and 1 g of flavor were dissolved in water, and water was added thereto to the total volume to 370 g. The resulting mixture was sterilized at 120° C. for three seconds to give a syrup solution. The bacterial suspension and the syrup solution were mixed and then poured into a tetra brick container, whereby a fermented milk product having: pH of 5.6; acidity of 3.4; nonfat milk solid content of 8.7%; and milk fat content of 3.2% was obtained (the initial bacterial count of *Bifidobacterium breve* YIT 12272 strain was $9.5 \times 10^8$ CFU/mL).

The fermented milk product thus obtained was stored at 10° C. for 14 days, in which the survival rate of *Bifidobacterium breve* YIT 12272 strain was found to be 30%. Also, the fermented milk product thus obtained had excellent taste.

Example 6

Production of Fermented Milk Foods and Drinks

Into 90 g of water, 25 g of defatted milk powder was dissolved, followed by sterilization at 120° C. for 3.5 seconds. Subsequently, 2% of *Bifidobacterium breve* YIT 12272 strain and 0.01% of *Lactococcus* lactis were inoculated and cultured at 37° C. until the pH reached 4.4. The resulting mixture was homogenized at 15 MPa to give 115 g of bacterial suspension A. Also, 60 g of defatted milk powder and 0.25 g of milk peptide were dissolved in water, and water was added thereto to the total volume to 330 g. The resulting mixture was sterilized at 120° C. for 3.5 seconds, and 0.5% of *Streptococcus* thermophilus was inoculated. The bacteria were cultured at 37° C. until the pH reached 4.3, and then the resulting mixture was homogenized at 15 MPa to give 330 g of Bacterial suspension B. Meanwhile, 47 g of maltitol, 29 g of polydextrose, 14 g of galactooligosaccharide syrup, 3.5 g of emulsified iron, 3 g of pectin, 1 g of collagen peptide, 0.3 g of vitamin B mix, and 0.1 g of aspartame were dissolved in water, 1 g of flavor and 1 g of vitamin E oil were further added, and then water was added to the total volume to 555 g. The resulting mixture was sterilized at 120° C. for three seconds to give a syrup solution. The bacterial suspensions A and B and the syrup solution were mixed and then filled into a tetra brick container, whereby a fermented milk product having: pH of 4.4; acidity of 7.5; nonfat milk solid content of 8.10; and milk fat content of 0.1% was obtained (the initial bacterial count of *Bifidobacterium breve* YIT 12272 strain was $8.8 \times 10^8$ CFU/mL).

The fermented milk product thus obtained was stored at 10° C. for 16 days, in which the survival rate of *Bifidobacterium breve* YIT 12272 strain was found to be 34%. Also, the fermented milk product thus obtained had excellent flavor.

Example 7

Production of Fermented Milk Foods and Drinks

Into 198 g of water, 58 g of defatted milk powder was dissolved, followed by sterilization at 120° C. for 3.5 seconds. Subsequently, 1% of *Bifidobacterium breve* YIT 12272 strain, 0.2% of *Lactococcus* lactis, and 0.01% of *Streptococcus* thermophilus were inoculated and cultured at 37° C. until the pH reached 4.5. The resulting mixture was homogenized at 15 MPa to give 256 g of bacterial suspension. Meanwhile, 25 g of galactooligosaccharide syrup, 16 g of lactitol, 16 g of palatinose, 3 g of pectin, and 0.05 g of sucralose were dissolved in water, and 1 g of flavor and water were further added to the total volume to 744 g. The resulting mixture was then sterilized at 120° C. for three seconds to give a syrup solution. The bacterial suspension and the syrup solution were mixed and then filled into a tetra brick container, whereby a fermented milk drink having; pH of 4.4: acidity of 5.3; nonfat milk solid content of 5.5%; and milk fat content of 0.1% was obtained (the initial bacterial count of *Bifidobacterium breve* YIT 12272 strain was $1.3 \times 10^9$ CFU/mL).

The fermented milk drink thus obtained was stored at 10° C. for 23 days. As a result, the survival rate of *Bifidobacterium breve* YIT 12272 strain was found to be 41%. Also, the fermented milk drink thus obtained had excellent taste.

Example 8

Production of Fermented Milk Foods and Drinks 58 g of whole milk powder, 42 g of defatted milk, and 0.02 g of milk peptide were dissolved in 487 g of water, followed by sterilization at 135° C. for three seconds. Into the resulting mixture, the starters of *Bifidobacterium breve* YIT 12272 strain and *Lactobacillus acidophilus* were each inoculated by 0.5% and 1.0%, respectively. The resulting mixture was then cultured at 33° C. until the pH reached 5.3, and then homogenized at 15 MPa to give 587 g of a bacterial suspension.

Meanwhile, 98 g of palatinose, 8 g of carrot juice, and 1 g of flavor were dissolved in water, and water was further added to the total volume to 413 g. The resulting mixture was sterilized at 120° C. for three seconds to give a syrup solution.

The bacterial suspension and the syrup solution were mixed and then filled into a tetra brick container, whereby fermented milk product having: pH of 5.6; acidity of 2.9; nonfat milk solid content of 8.1%; and milk fat content of 1.4% was obtained (the initial bacterial count of *Bifidobacterium breve* YIT 12272 strain was $9.5 \times 10^8$ CFU/mL).

The fermented milk product thus obtained was stored at 10° C. for 14 days, and the survival rate of *Bifidobacterium breve* YIT 12272 strain was found to be 30%. Also, the fermented milk product thus obtained had excellent taste.

Example 9

Production of Tablets

Each of the ingredients shown below was mixed in accordance with the following formulation, and the resulting mixture was subjected to granulation, drying, and granule size adjustment, followed by tableting, whereby tablets were produced.

| (Formulation) | (mg) |
|---|---|
| Dried bacterial cell of the present invention[1] | 20 |
| Microcrystalline cellulose | 100 |
| Lactose | 80 |
| Magnesium stearate | 0.5 |
| Methylcellulose | 12 |

[1] Produced by lyophilizing the live bacterial cell of *Bifidobacterium breve* YIT 12272 strain.

1) Produced by lyophilizing the live bacterial cell of *Bifidobacterium breve* YIT 12272 strain.

Example 10

Production of Soft Drinks

Each of the ingredients shown below was blended in accordance with an ordinary method based on the following formulation. The resulting mixture was homogenized to give soft drinks. The soft drinks thus obtained were put into brown bottles and sealed with an aluminum cap, followed by heat treatment. The soft drinks thus obtained were favorable in both external appearance and taste, and also had good storage stability.

| (Formulation) | (g) |
|---|---|
| Dried bacterial cell of the present invention[1] | 5 |
| Flavor | 0.8 |
| Water | 100 |
| Reduced saccharified starch | 24 |
| Fructose | 18 |

[1] Produced by lyophilizing the live bacterial cell of *Biofidobacterium breve* YIT 12272 strain.

1) Produced by lyophilizing the live bacterial cell of *Bifidobacterium breve* YIT 12272 strain.

Example 11

Production of a Bacterial Strain-Specific Primer by Random Amplified Polymorphic DNA (RAPD) Method Using 62 strains of the bacteria belonging to *Bifidobacterium breve*, DNA was extracted from the bacterial cell and RAPD method was applied by performing PCR in accordance with the following procedure to search for a nucleotide sequence specific for YIT 12272.

(1) Extraction of DNA from Bacterial Cell

Sixty-two strains of the bacteria belonging to *Bifidobacterium breve* (*Bifidobacterium breve* YIT 4014$^T$, YIT 4015, YIT 4023, YIT 4024, YIT 4043, YIT 4049, YIT 4063, YIT 4064, YIT 12272, and 53 other strains) were cultured using a GAM medium (Nissui Pharmaceutical Co., Ltd.) supplemented with 1% glucose, for 24 hours at 37° C. under anaerobic conditions. Bacterial suspension (0.5 mL) was centrifuged, a supernatant was removed, and 0.25 mL of a DNA extraction buffer (100 mM Tris-HCl, 40 mM EDTA, pH 9.0), 0.05 mL of 10% SDS, 0.5 mL of TE-saturated phenol, and 0.7 g of glass beads (the diameter of 0.1 mm) were added. The mixture was vigorously shaken to disrupt the bacterial cell. Then, 0.15 mL of 3 M sodium acetate was added and the mixture was centrifuged, and a supernatant was transferred to other tubes. After precipitation with isopropanol and washing with 700 ethanol, the product thus obtained was air dried and lastly dissolved in 0.1 mL of a TE buffer (10 mM Tris-HCl (pH8.0), 1 mM EDTA).

(2) RAPD Method

The RAPD method was carried out using 27 kinds of random primers (Table 7). A reaction liquid had a total volume of 20 μL containing 10 mM Tris-HCl (pH 8.3), 50 mM KCl, 1.5 mM MgCl$_2$, 200 μM dNTP mixture, 1.5 μM random primer, 1.5 U of Taq DNA polymerase (the product of Takara Bio Inc.), and 10 ng of template DNA. PCR reactions were carried out using DNA thermal cycler PTC200 (MJ Research, Inc.), in which the PCR reaction included the following steps; 94° C. for 120 seconds, six cycles of (94° C. for 20 seconds, 36° C. for 30 seconds, 72° C. for 90 seconds), 30 cycles of (94° C. for 20 seconds, 36° C. for 30 seconds, and 72° C. for 90 seconds), and 72° C. for 180 seconds. The amplification product thus obtained was subjected to electrophoresis at 50 V on a 1.5% agarose gel. Then, the gel was stained with ethidium bromide for confirmation under UV irradiation.

TABLE 7

Sequence of a random primer for RAPD method

| Primer name | Sequence (5' . . . 3') |
|---|---|
| p1001 | GTGAAGTAGG (SEQ ID NO (4)) |
| p1002 | CAATAGCCGT (SEQ ID NO (5)) |
| p1003 | CAGTACCCAC (SEQ ID NO (6)) |
| p1004 | AGGTAACCGT (SEQ ID NO (7)) |
| p1005 | CAGTACCTTC (SEQ ID NO (8)) |
| p1006 | GGTTAAAGCC (SEQ ID NO (9)) |
| p1007 | TCGACGATAG (SEQ ID NO (10)) |
| p1008 | AGCCAACGAA (SEQ ID NO (11)) |
| p1009 | GTTGCGGTCC (SEQ ID NO (12)) |
| p1010 | TGCGACTTAC (SEQ ID NO (13)) |
| p1011 | GTAGACAAGC (SEQ ID NO (14)) |
| p1248 | TGCCGAATTC (SEQ ID NO (15)) |
| p1249 | CGAACTAGAC (SEQ ID NO (16)) |
| p1250 | GGCTTAACAC (SEQ ID NO (17)) |
| p1251 | AAGACTGTCC (SEQ ID NO (18)) |
| p1252 | GCGGAAATAG (SEQ ID NO (19)) |
| p1254 | CCGCAGCCAA (SEQ ID NO (20)) |
| p1255 | CCGATCTAGA (SEQ ID NO (21)) |
| p1280 | GAGGACAAAG (SEQ ID NO (22)) |
| p1281 | AACGCGCAAC (SEQ ID NO (23)) |
| p1282 | GACGACTATC (SEQ ID NO (24)) |
| p1284 | GTCAACGAAG (SEQ ID NO (25)) |
| p1285 | AGCCAGTTTC (SEQ ID NO (26)) |
| p1287 | CGCATAGGTT (SEQ ID NO (27)) |
| p1288 | GGGGTTGACC (SEQ ID NO (28)) |
| p1289 | ACTTGCATCC (SEQ ID NO (29)) |
| p1292 | CCCGTCAGCA (SEQ ID NO (30)) |

(3) Cloning

Comparing RAPD band patterns of 62 strains of the bacteria belonging to *Bifidobacterium breve*, a PCR amplification product which was found to be specific for YIT 12272 was cloned using TA cloning kit (the product of Invitrogen Corporation) in accordance with the attached manual. That is, the PCR amplification product was inserted into a pCR2.1 vector and introduced into *Escherichia coli* for transformation. Thereafter, the transformed *E. coli* was inoculated in a Luria Bertani (LB) agar medium containing X-gal and 50

μg/mL ampicillin and cultured. Then, the white colony-forming bacteria thus obtained were proliferated in the LB liquid medium, and therefrom DNA was extracted to obtain cloned DNA. In accordance with the standard method, the DNA nucleotide sequence of the PCR amplification product was determined by a dye terminator method (FIG. 1).

(4) Production of a Bacterial Strain-Specific Primer and Confirmation of its Specificity Among the DNA nucleotide sequences of the PCR amplification product specific for YIT 12272 obtained by cloning, a sequence which was most specific for YIT 12272 and had high PCR reactivity was selected to produce a YIT 12272-specific primer. The sequence of the primer was shown in Table 8. Using this YIT 12272-specific primer, PCR was carried out on DNA extracted from a total of 144 bacterial strains including 62 bacterial strains of the bacteria belonging to *Bifidobacterium breve* and 82 strains of 78 species of 12 genera of bacteria frequently isolated from human intestinal tract (Table 9) to confirm specificity. Using a reaction mixture having a total volume of 20 μl, containing 10 mM Tris-HCl (pH 8.3), 50 mM KCl, 1.5 mM MgCl$_2$, 200 μM dNTP mixture, 0.3 μM primer, 0.5 U of Taq DNA polymerase, and 10 ng of template DNA, PCR reactions were carried out, in which the PCR reaction included the following steps; 94° C. for 120 seconds, 32 cycles of (94° C. for 20 seconds, 60° C. for 10 seconds, and 72° C. for 20 seconds), and 72° C. for 180 seconds. The amplification product thus obtained was subjected to electrophoresis at 100 V on a 1.5% agarose gel. Then, the gel was stained with ethidium bromide for confirmation under UV irradiation. As a result, the YIT 12272-specific primer thus produced was confirmed to be specific for *Bifidobacterium breve* YIT 12272.

TABLE 8

Sequence of the YIT 12272-specific primer (pBbrY)

| SEQ ID NO | Target organism | Primer name | Sequence (5' . . . 3') |
|---|---|---|---|
| 1 | *B. breve* YIT 12272 | pBbrY-F | ATG GCA AAA CCG GGC TGA A |
| 2 | | pBbrY-R | GCG GAT GAG AGG TGG G |

TABLE 9

| Bacterial strain used | |
|---|---|
| *Bacteroides* spp. | *Bacteroides distasonis* YIT 6162$^T$, *B. fragilis* YIT 6158$^T$, *B. ovatus* YIT 6161$^T$, *B. thetaiotaomicron* YIT 6163$^T$, *B. uniformis* YIT 6164$^T$, *B. vulgatus* YIT 6159$^T$ |
| *Bifidobacterium* spp.(Except *B. breve*) | *Bifidobacterium adolescentis* YIT 4011$^T$, *B. angulatum* YIT 4012$^T$, *B. animalis* subsp. *animalis* YIT 4044$^T$, *B. animalis* subsp. *lactis* YIT 4121$^T$, *B. asteroides* YIT 4033$^T$, *B. bifidum* YIT 4039$^T$, *B. boum* YIT 4091$^T$, *B. catenulatum* YIT 4016$^T$, *B. choerinum* YIT 4067$^T$, *B. coryneforme* YIT 4092$^T$, *B. cuniculi* YIT 4093$^T$, *B. dentium* YIT 4017$^T$, *B. gallicum* YIT 4085$^T$, *B. gallinarum* YIT 4094$^T$, *B. indicum* YIT 4083$^T$, *B. longum* subsp. *infantis* YIT 4018$^T$, *B. longum* subsp. *longum* YIT 4021$^T$, *B. longum* subsp. *suis* YIT 4082$^T$, *B. magnum* YIT 4098$^T$, *B. merycicum* YIT 4095$^T$, *B. minimum* YIT 4097$^T$, *B. pseudocatenulatum* YIT 4072$^T$, *B. pseudolongum* subsp. *globosum* YIT 4101$^T$, *B. pseudolongum* subsp. *pseudolongum* YIT 4102$^T$, *B. pullorum* YIT 4104$^T$, *B. ruminantium* YIT 4105$^T$, *B. saeculare* YIT 4111$^T$, *B. subtile* YIT 4116$^T$, *B. thermophilum* YIT 4073$^T$ |
| *Clostridium* spp. | *Clostridium celatum* YIT 6056$^T$, *C. perfringens* YIT 6050$^T$ |
| *C. aerofaciens* | *Collinsella aerofaciens* YIT 10235$^T$ |
| *Enterococcus* spp. | *Enterococcus faecalis* YIT 2031$^T$, *E. faecium* YIT 2032$^T$ |
| *E. coli* | *Escherichia coli* YIT 6044$^T$ |
| *Eubacterium* spp. | *Eubacterium biforme* YIT 6076$^T$, *E. rectale* YIT 6082$^T$ |
| *Lactobacillus* spp. | *Lactobacillus acidophilus* YIT 0070$^T$, *L. amylophilus* YIT 0255$^T$, *L. amylovorus* YIT 0211$^T$, *L. bifermentans* YIT 0260$^T$, *L. brevis* YIT 0076$^T$, *L. buchneri* YIT 0077$^T$, *L. casei* YIT 0180$^T$, YIT 9029, *L. coryniformis* subsp. *coryniformis* YIT 0237$^T$, *L. crispatus* YIT 0212$^T$, *L. delbrueckii* subsp. *delbrueckii* YIT 0080$^T$, *L. delbrueckii* subsp. *lactis* YIT 0086$^T$, *L. delbrueckii* subsp. *bulgaricus* YIT 0181$^T$, *L. fermentum* YIT 0081$^T$, *L. gallinarum* YIT 0218$^T$, *L. gasseri* YIT 0192$^T$, *L. helveticus* YIT 0083$^T$, *L. johnsonii* YIT 0219$^T$, *L. malefermentans* YIT 0271$^T$, *L. oris* YIT 0277$^T$, *L. parabuchneri* YIT 0272$^T$, *L. paraplantarum* YIT 0445$^T$, *L. pentosus* YIT 0238$^T$, *L. plantarum* YIT 0102$^T$, *L. pontis* YIT 0273T, *L. reuteri* YIT 0197$^T$, *L. rhamnosus* YIT 0105$^T$, *L. sakei* YIT 0247$^T$, *L. salivarius* subsp. *salivarius* YIT 0104$^T$, *L. sharpeae* YIT 0274$^T$, *L. vaginalis* YIT 0276$^T$, *L. zeae* YIT 0078$^T$ |
| *Lactococcus* spp. | *Lactococcus garviae* YIT 2071$^T$, *L. lactis* subsp. *cremoris* YIT 2007$^T$, *L. lactis* subsp. *lactis* YIT 2008$^T$, *L. lactis* subsp. *hordiniae* YIT 2060$^T$, *L. plantarum* YIT 2061$^T$, *L. raffinolactis* YIT 2062$^T$ |
| *Propionibacterium* | *Propionibacterium acnes* YIT 6165$^T$ |
| *Ruminococcus* spp. | *Ruminococcus bromii* YIT 6078$^T$, *R. lactaris* YIT 6084$^T$, *R. productus* YIT 6141$^T$ |
| *Streptococcus* spp. | *Streptococcus thermophilus* YIT 2001, YIT 2021, YIT 2037$^T$ |

Example 12

Detection of Live YIT 12272 by PCR Method (1) Optimization of a Membrane-Permeable Dye Ethidium monoazide (EMA) and propidium monoazide (PMA), which were a membrane-permeable dye, were used for *Bifidobacterium breve* YIT 12272. Using a liquid medium with GAM+1% glucose, to each of untreated YIT 12272 which had been cultured for 24 hours at 37° C. under anaerobic conditions (live bacteria), dead cells thereof obtained by heating the bacteria at 80° C. for 10 minutes, or dead cells thereof obtained by continuously culturing the bacteria for 10 days at 37° C., the dye was added to the final concentrations of EMA and PMA of 240 μM and 50 μM, respectively. After keeping warm for five minutes at room temperature, the bacteria were irradiated by light for two minutes using two 500 W halogen lamps at a distance of 20 cm under the lamp. Thereafter, DNA was extracted from each of bacterial cells, and YIT 12272 was quantified by quantitative PCR using the YIT 12272-specific primer. (As a quantitative PCR method, the method described in International Journal of Food Microbiology (2008) Vol. 126, p. 210 to 215 was used.) As a result, while both EMA and PMA inhibited PCR amplification in dead bacterial cells, EMA also inhibited PCR amplification in live bacteria. Based on that PMA inhibited PCR amplification in dead bacteria without inhibiting PCR amplification in live YIT 12272, it was found that PMA was suitable for detection and quantification of live YIT 12272 by quantitative PCR. [FIG. 2]

Figure 3:
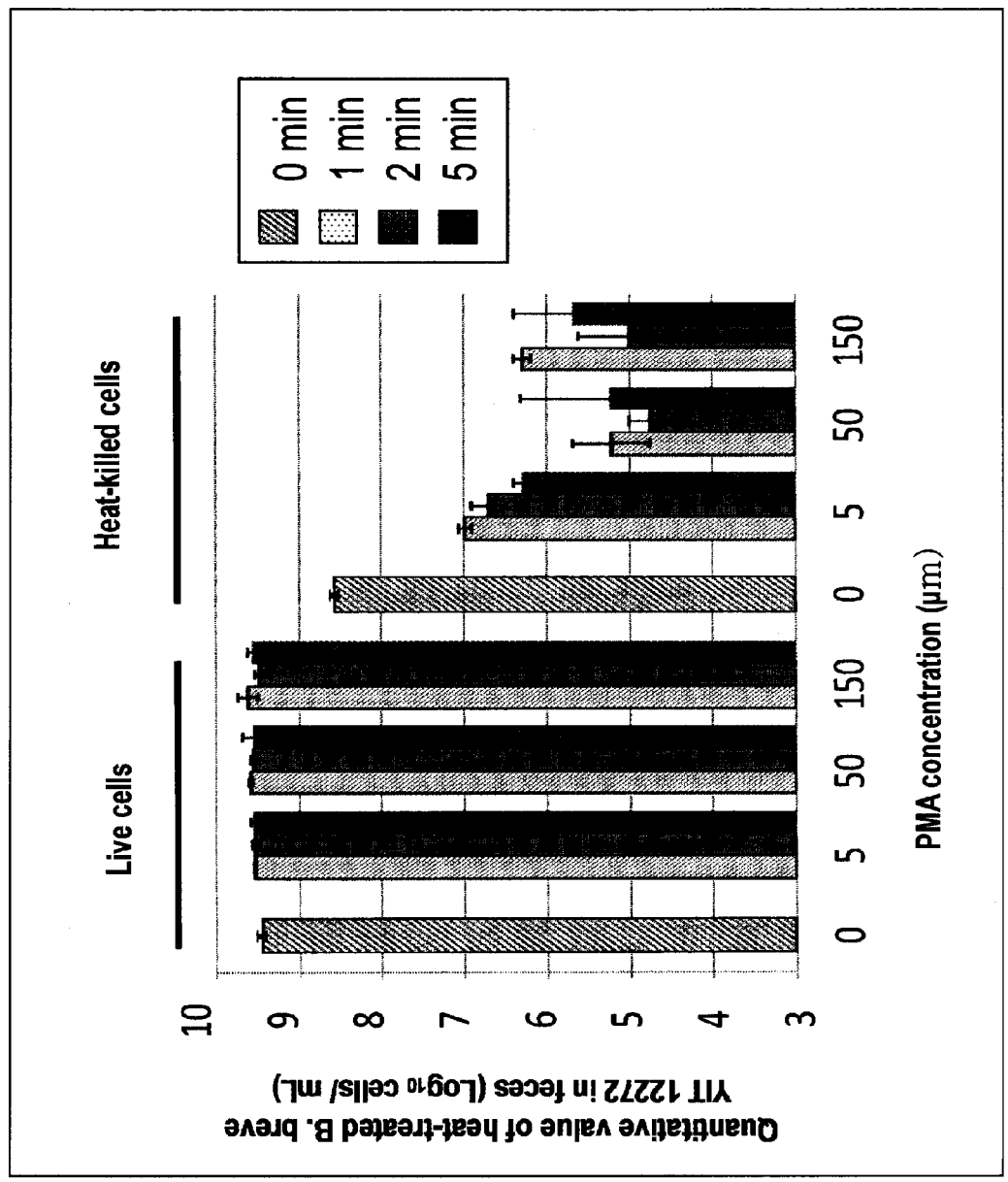
FIG. 3 shows the optimum conditions for PMA treatment.

In order to optimize the PMA treatment, quantitative PCR was carried out using the YIT 12272-specific primer, and live bacteria and heat-killed bacterial cells of YIT 12272 treated with various PMA concentrations (5 µM, 50 µM, and 150 µM) and light irradiation time (one, two, and five minutes). As a result, it was found that light irradiation time did not affect the PMA treatment, and that the treatment with low concentration (5 µM) and high concentration (150 µM) of PMA exhibited a weaker inhibitory effect on PCR amplification in the heat-killed bacterial cell, compared to the treatment with 50 µM PMA (FIG. 3). Accordingly, it was found that treatment with 50 µM PMA and two minutes of light irradiation was suitable for the PMA treatment to be applied on YIT 12272.

(2) Detection and Quantification of Live YIT 12272 in Feces

Figure 4:
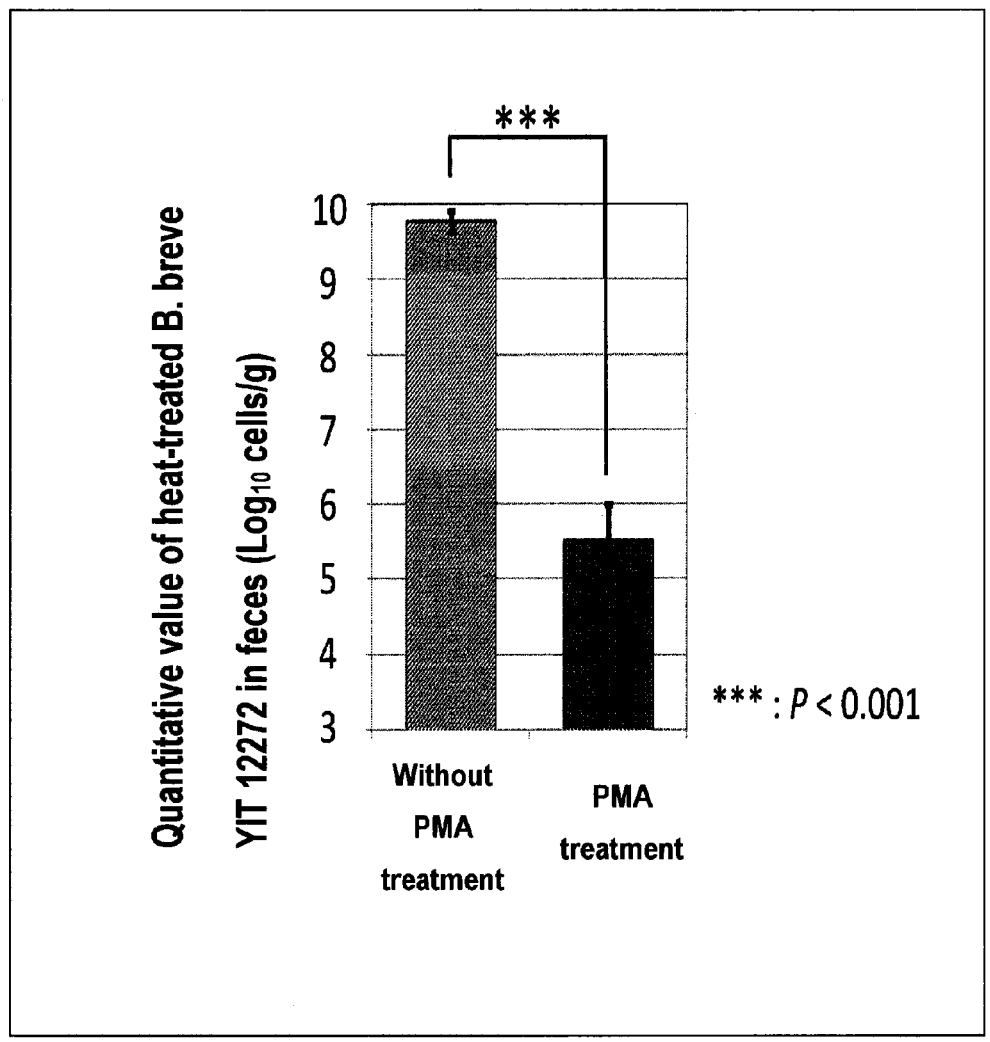
FIG. 4 shows the shift in the quantitative value of heat-treated YIT 12272 in the feces by PMA treatment.
Figure 5:
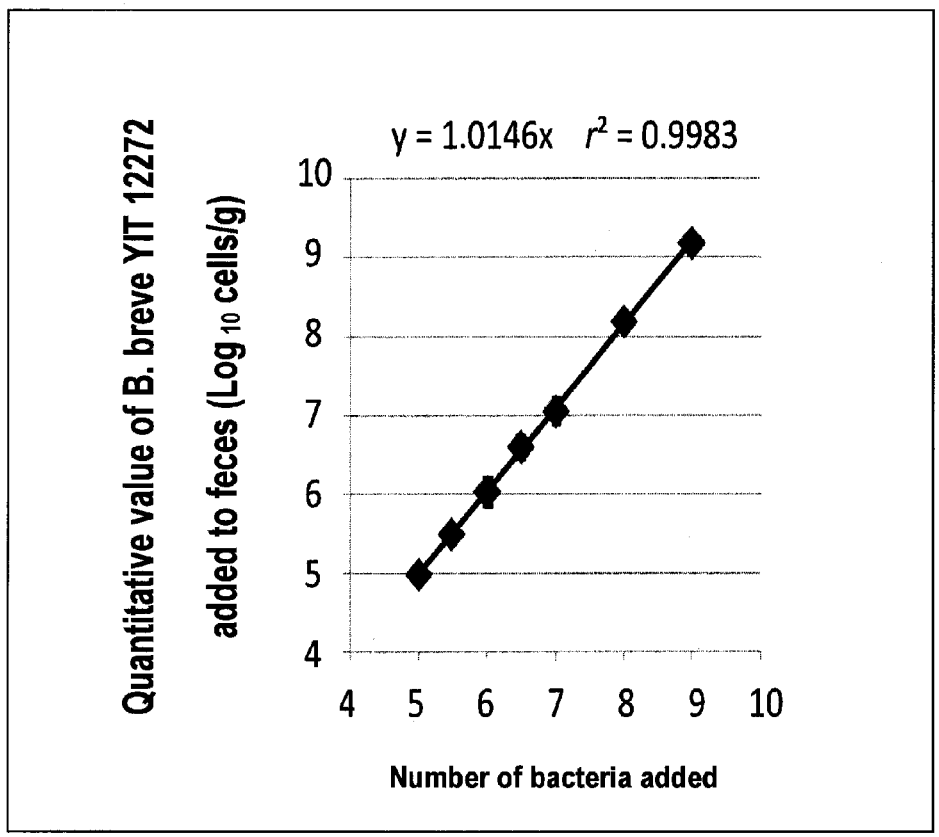
FIG. 5 shows a relationship between the viable bacterial count of live YIT 12272 added to the feces and the quantitative value of YIT 12272 obtained by quantitative PCR (with PMA treatment).

Feces in which the absence of YIT 12272 was confirmed by a selective medium and quantitative PCR using the YIT 12272-specific primer was prepared. To the feces, heat-killed bacterial cells of YIT 12272 were added, followed by the PMA treatment (50 µM PMA and two minutes of light irradiation). As a result, it was found that PCR amplification in the heat-killed bacterial cells of YIT 12272 in feces was inhibited, and the quantitative value of the dead bacteria of YIT 12272 was decreased to approximately one-twenty thousandth (FIG. 4). In contrast, live YIT 12272 which had been cultured for 24 hours was added to the feces and the PMA treatment was carried out, and YIT 12272 was quantified by quantitative PCR using the primer specific for YIT 12272. As a result, the PMA treatment did not inhibit PCR amplification in viable YIT 12272, resulting that, when YIT 12272 is present in an amount of $10^5$ or more per gram of feces, viable YIT 12272 can be accurately quantified (FIG. 5). Herein, the viable bacterial count of YIT 12272 can be calculated by the following formula 3.

(Symbol)
PCR quantitative value of YIT 12272 without PMA treatment: X cells/g
PCR quantitative value of YIT 12272 subjected to PMA treatment: Y cells/g
The viable bacterial count of YIT 12272 in a sample: L cells/g
The dead bacterial count of YIT 12272 in a sample: D cells/g $X=L+D$  Formula 1:

$Y=L+D/20000$  Formula 2:

(Formula 3 is derived by Formulae 1 and 2): $L=(20000Y-X)/19999$  Formula 3

The following method was used for extraction of DNA from feces. Using an anaerobic diluting solution (Table 10), a 10-fold diluted solution of feces was prepared. Then, 0.2 mL of the solution was centrifuged and a supernatant was removed, followed by re-suspension in 1.0 mL of a PBS buffer. The above washing operation was repeated three times. Thereafter, the pellet of feces thus obtained was stored at −80° C. until the extraction of the nucleic acid. The lyophilized pellet of feces was thawed, and thereto 0.6 mL of an ASL buffer (QIAGEN) was added, followed by heating at 70° C. for five minutes. Subsequently, 0.5 mL of TE-saturated phenol and 0.7 g of glass beads with a diameter of 0.1 mm were added, and the resulting mixture was vigorously shaken at 6.5 m/s for 30 seconds using FastPrep FP120 (Bio101, Inc.). Then, 0.1 mL of 3 M sodium acetate was added and a supernatant was obtained by centrifugation. Into 0.7 mL of the supernatant, 0.7 mL of an ASL buffer and Inhibit EX tablets (QIAGEN) were added. The resulting mixture was thoroughly mixed and centrifuged to obtain a supernatant. To 0.55 mL of the supernatant, 0.55 mL of an AL buffer (QIAGEN) and 0.55 mL of 100% ethanol were added, followed by stirring. Subsequently, all the resulting mixture was passed through QIAmp spin column (QIAGEN) to allow DNA to adsorb to the column. After washing the column, 0.1 mL of an AE buffer (QIAGEN) was added and the resulting solution was centrifuged, whereby DNA was collected.

TABLE 10

Composition of anaerobic diluting solution

| Component | composition (g/L) |
|---|---|
| $KH_2PO_4$ | 0.225 |
| $K_2HPO_4$ | 0.225 |
| NaCl | 0.45 |
| $(NH_4)_2SO_4$ | 0.225 |
| $CaCl_2$ | 0.0225 |
| $MgSO_4$ | 0.0225 |
| L-Cysteine hydrochloride monohydrate | 0.5 |
| Resazurin | 0.001 |
| Bacto agar | 0.5 |
| Tween 80 | 0.5 |

(3) Detection and Quantification of Live YIT 12272 in Feces in an Oral Ingestion Test A study was conducted in which healthy adults who had been prohibited from taking food products containing live bacteria for three weeks were subject to ingestion of one pack (100 mL) of fermented milk product of Example 6 (containing YIT 12272 in an amount of $10^{10.5}$/pack) daily continuously for 10 days.

(3-1) Detection of Live YIT 12272 by a Combination of Selective Medium and the Primer Specific for YIT 12272

Feces were collected from the subjects before and after ingesting the fermented milk product containing YIT 12272 of Example 6 and subjected to a 10-fold serial dilution using a dilution buffer (PBS). From the resulting solution, 100 µL was applied to a YIT 12272-selective medium (T-CBPC, Table 11), followed by anaerobic culture at 37° C. for 72 hours to form colony. The colonies thus obtained were anaerobically cultured at 37° C. for 24 hours in a 1% glucose-added GAM liquid medium (Nissui Pharmaceutical Co., Ltd.), whereby bacterial cells were obtained. DNA was extracted from the bacterial cells, and PCR was carried out using the DNA thus obtained as a template and the primer specific for YIT 12272. Also, some of the bacterial strains were subjected to bacterial strain identification by RAPD test. As a result, the outcomes of identification of YIT 12272 by both of the above methods perfectly matched. Up until now, to determine a colony formed on the selective medium as YIT 12272, time-consuming and complex RAPD assay and ELISA (Enzyme-Linked-ImmunoSorbent Assay) using a YIT 12272-specific monoclonal antibody have been necessary. However, it was shown that use of the primer specific for YIT 12272 enabled rapid and simple determination of YIT 12272.

TABLE 11

Composition of YIT 12272 selective medium (T-CBPC)

| Component | Composition (/L) |
|---|---|
| TOS propionate agar medium (Yakult Pharmaceutical Industry Co., Ltd.) | 62.5 g |
| Antibiotic solution * | 50 mL |

* Added after autoclaving at 115° C. for 15 min.
Containing the following per 50 mL
Carbenicillin disodium salt and 0.001 g Streptomycin sulfate salt 5000000 U (3-2) Quantification of Live YIT 12272 in Feces In order to detect live YIT 12272 in feces collected from the subjects before and after ingesting the fermented milk product containing YIT 12272 of Example 6, dissolved pellets of feces were suspended in 0.5 mL of PBS, and thereto 1.4 µL of a 20 mM PMA solution was added (final concentration of 50 µM). The resulting mixture was gently stirred and stored in the dark for five minutes. Subsequently, the mixture was irradiated with intense light for two minutes using a halogen lamp and centrifuged, and a supernatant was removed. DNA was extracted from PMA-treated feces, and live YIT 12272 in feces was quantified by combining quantitative PCR using the primer specific for YIT 12272. Also, the total bacterial count of YIT 12272 including dead cells in feces was simultaneously quantified without PMA treatment. The results thus obtained are shown in Table 12 together with CFU of YIT 12272 obtained using a T-CBPC agar selective medium. YIT 12272 was not detected in feces collected from the subjects before ingesting the fermented milk product containing YIT 12272 by either the culture method or the quantitative PCR using the primer specific for YIT 12272. In contrast, the total number (viable and dead) of *B. breve* YIT 12272 detected by qPCR without PMA treatment was $10^{8.1 \pm 0.8}$, viable *B. breve* YIT 12272 detected by qPCR with PMA treatment was $10^{7.5 \pm 1.0}$, and $10^{6.9 \pm 1.5}$ CFU of YIT 12272 was detected by using strain-specific selective medium, per gram of the feces collected from the subjects who completed the ingestion. Further, because the quantitative value of the PMA-treated dead bacterial cell obtained by PCR was sufficiently small, the viable bacterial count of YIT 12272 calculated by Formula 3 was equal to the bacterial count obtained by the quantitative PCR after PMA treatment (Table 12). Accordingly, it was confirmed that use of PMA treatment and quantitative PCR enabled determination of the viable bacterial count of YIT 12272.

TABLE 12

Bacterial count of YIT 12272 in feces collected from the subjects before and after ingesting the fermented milk product containing YIT 12272

| | $Log_{10}$ cells or CFU/g Feces | | | | | |
|---|---|---|---|---|---|---|
| | Before ingestion | | | After ingestion | | |
| | Quantitative PCR | | | Quantitative PCR | | |
| Sample | Without PMA treatment (Live cell + dead cell) | PMA treatment (Live cell) | CFU | Without PMA treatment (Live cell + dead cell) | PMA treatment (Live cell) | CFU |
| a | <5.0[a] | <5.0 | <2.0[a] | 8.5 | 8.4 | 7.9 |
| b | <5.0 | <5.0 | <2.0 | 6.7 | <5.0 | 3.3 |
| c | <5.0 | <5.0 | <2.0 | 8.5 | 8.3 | 7.4 |
| d | <5.0 | <5.0 | <2.0 | 8.8 | 8.4 | 7.9 |
| e | <5.0 | <5.0 | <2.0 | 6.4 | 5.3 | 4.8 |
| f | <5.0 | <5.0 | <2.0 | 8.4 | 7.9 | 7.6 |
| g | <5.0 | <5.0 | <2.0 | 8.4 | 7.7 | 6.9 |
| h | <5.0 | <5.0 | <2.0 | 9.1 | 8.8 | 8.3 |
| I | <5.0 | <5.0 | <2.0 | 8.2 | 7.1 | 6.8 |
| j | <5.0 | <5.0 | <2.0 | 8.2 | 8.0 | 7.2 |
| k | <5.0 | <5.0 | <2.0 | 8.5 | 8.1 | 7.5 |
| Average[b] | <5.0 | <5.0 | <2.0 | 8.1 | 7.5 | 6.9 |
| S.D.[b] | — | — | — | 0.8 | 1.0 | 1.5 |

[a]The detection limit of YIT 12272 by quantitative PCR is $10^5$ cells/gram feces and that by the culture method is $10^2$ CFU.
[b]If any sample was present below the detection limit, an average value and S.D of the sample were calculated based on the bacterial count of the detection limit.

Up until now, a method of detecting and quantifying YIT 12272 in feces was carried out by allowing the bacteria to form a colony on the selective medium, and a test for confirming a colony as YIT 12272 has required considerable work and time. Also, considering that the selective medium contain a high-concentration of antibiotic, a possibility that damaged bacteria cannot undergo division, for which live YIT 12272 is underestimated, is pointed out. Quantitative PCR using the primer specific for YIT 12272 of the present invention enables quantification of all of YIT 12272 in feces regardless of being dead or alive. Further, only live YIT 12272 in feces could be rapidly and simply quantified by combining PMA, which is a membrane-permeable dye.

Example 13

Ingested Bacteria-Recovery Test

Nineteen healthy adults in their twenties to fifties were randomly divided into two groups, and after seven days of observation (observation period), the subjects ingested one pack (100 mL) of either fermented milk product prepared by using YIT 12272 strain (test drink) or fermented milk product prepared by using YIT 10001 strain instead of YIT 12272 (control drink), both of which were produced in accordance with the method described in Example 6, daily for seven days (ingestion period 1). After 10 days of interruption (interruption period), subjects ingesting either the test drink or the control drink were crossovered, and ingestion was further continued for seven days (ingestion period 2). Feces were collected on the day following the final day of the observation period, each ingestion periods, and the interruption period. It is to be noted that the subjects were prohibited from ingesting any fermented milk products or probiotic products other than the test drink or the control drink during the test period. Also, the bacterial counts of the *Bifidobacterium* in the test drink and the control drink were 6.8 to $8.9 \times 10^8$ CFU/mL and 2.9 to $4.2 \times 10^8$ CFU/mL, respectively.

In accordance with Example 12, using the T-CBPC agar selective medium, the CFU of the ingested bacteria in feces (YIT 12272 strain or YIT 10001 strain) was obtained. Using RAPD method or the primer specific for YIT 12272 strain as shown in Table 8, a qualitative test of bacterial strain was conducted.

Although the ingested bacteria were not detected in feces collected from any of the subjects before ingesting the fermented milk product, the bacterial counts of the ingested bacteria in the test drink-ingestion group and the control drink-ingestion group after ingestion were 7.3±0.8 Log CFU/g and 5.9±1.1 Log CFU/g, respectively, showing that the bacterial count was significantly higher in the test drink-ingestion group than in the control drink-ingestion group (Table 13). It is to be noted that no adverse event associated with the ingestion of either the test drink or the control drink was observed during the study period.

TABLE 13

The bacterial count of ingested bacteria in feces

|  | Before ingestion | After ingestion |
|---|---|---|
| Test drink-ingestion group (n = 19) |  |  |
| The bacterial count of the ingested bacteria detected (Log CFU/g) | ND | 7.3 ± 0.8## |
| Control drink-ingestion group (n = 19) |  |  |
| The bacterial count of the ingested bacteria detected (Log CFU/g) | ND | 5.9 ± 1.1 |

$p < 0.01$ Compared with the control drink-ingestion group (independent two group t-test)
ND: Below detection limit ($10^2$ CFU)

It was revealed that, by ingestion of the present fermented milk product, both of the YIT 12272 strain and YIT 10001 strain were collected alive from feces; however, the bacterial count of YIT 12272 strain was significantly higher than that of YIT 10001. It was considered that this result reflected that YIT 12272 strain had favorable viability in a product, and at the same time its resistance against artificial gastric juice and artificial bile/intestine fluid was enhanced.

Example 14

Test on the Intestine-Regulating Action 1

An open test was conducted in which 57 subjects aged 63 or older suffering from constipation or prone to constipation (three to five times of bowel movement/week, water content of the feces of less than 70%, 27 males and 30 females, average age of 68.7±5.4) ingested, after two weeks of observation period, one pack (100 mL) of the fermented milk product described in Example 8 daily for four weeks. In the final week of the observation period and the ingestion period, the condition of bowel movement and the property of the feces (the Bristol Stool Scale) were examined. It is to be noted that the subjects were prohibited from ingesting any milk fermented products or probiotic products other than the present fermented milk product during the test period. Also, the bacterial count of the *Bifidobacterium* in the present fermented milk product was $1 \times 10^8$ CFU/mL or more.

Compared with before ingestion, the number of bowel movements, the number of days having bowel movement, and the amount of feces were significantly increased after ingestion. Also, the score on the Bristol Stool Scale was significantly improved, and the hard feces were normalized (Table 14). It is to be noted that no adverse event associated with the ingestion of the present fermented milk product was observed during the test period. From the above results, it was confirmed that the present fermented milk product had an intestine-regulating action.

TABLE 14

Condition of bowel movement and property of feces during the observation period and the ingestion period

|  | Observation period | Ingestion period |
|---|---|---|
| Number of bowel movements (number of times/week) | 5.0 ± 1.7 | 6.2 ± 1.9** |
| Number of days having bowel movement (number of days/week) | 4.3 ± 1.2 | 5.2 ± 1.2** |
| Amount of feces (unit/week)[1] | 21.7 ± 9.7 | 27.4 ± 11.8** |
| Score on the fecal property[2] | 3.6 ± 0.9 | 3.8 ± 0.7# |

[1]a cylindrical shape of a diameter of 2 cm x a height of 5 cm was set as one unit.
[2]Based on the Bristol Stool Scale, the feces were assessed on a scale of one to seven: (1) separate lumps, (2) hard, (3) cracks on the surface, (4) smooth surface, (5) semi-solid, (6) muddy, and (7) liquid.
**$p < 0.01$ Compared with the observation period (related two-group t-test)
$p < 0.05$ Compared with the observation period (Wilcoxon's signed rank sum test)

Example 15

Test on the Intestine-Regulating Action 2

A placebo-controlled double-blind parallel-group comparison test was conducted, in which 75 female students prone to constipation (aged between 18 to 23, five or less bowel movements/week) ingested, after four weeks of observation period, one pack (100 mL) of either the fermented milk product described in Example 6 (the test group) or a placebo drink (unfermented milk without bacteria, galactooligosaccharide, and polydextrose, the placebo group) daily for four weeks. In the final week of the observation period and the ingestion period, the condition of bowel movement and the property of the feces (the Bristol Stool Scale) were examined. It is to be noted that the subjects were prohibited from ingesting any fermented milk products or probiotic products other than the present fermented milk or the placebo drink during the study period. Also, the bacterial count of the *Bifidobacterium* in the present fermented milk product was $1 \times 10^8$ CFU/mL or more.

Forty-four subjects in whom the water content of the feces was less than 70% were analyzed (Table 15). As a result, it was found that the test group showed a tendency of more frequent bowel movements in the ingestion period compared with the placebo group (p=0.081). Although no change was observed in the number of days having bowel movement between the ingestion period and the observation period in the placebo group, it significantly increased in the test group in the ingestion period compared with the observation period, and it was significantly higher in the test group compared with the placebo group in the ingestion period. Although the score on the fecal property did not change in the placebo group in the ingestion period compared with the observation period, the score significantly increased in the test group, indicating an improved fecal property. Also, in the ingestion period, the test group showed a tendency of having a higher score for the fecal property (P=0.070) compared with the placebo group. It is to be noted that no adverse event associated with the ingestion of the present fermented milk product or the placebo drink was observed during the study period. From the above results, it was confirmed that the present fermented milk product had an intestine-regulating action.

TABLE 15

Condition of bowel movement and property of feces during the observation period and the ingestion period

|  | Observation period | Ingestion period |
|---|---|---|
| Number of bowel movement (number of times/week) | | |
| Placebo group (n = 20) | 4.1 ± 1.2 | 4.2 ± 1.8 |
| Test group (n = 24) | 4.7 ± 1.7 | 5.5 ± 2.9[a] |
| Number of days having bowel movement (number of days/week) | | |
| Placebo group (n = 20) | 3.8 ± 1.2 | 3.6 ± 1.4 |
| Test group (n = 24) | 3.8 ± 1.0 | 4.6 ± 1.6*[#] |
| Score on the fecal property[1] | | |
| Placebo group (n = 20) | 3.0 ± 1.2 | 3.1 ± 0.9 |
| Test group (n = 24) | 3.2 ± 0.9 | 3.6 ± 0.7*[b] |

[1] Based on the Bristol Stool Scale, the feces were assessed on a scale of one to seven: (1) separate lumps, (2) hard, (3) cracks on the surface, (4) smooth surface, (5) semi-solid, (6) muddy, and (7) liquid.
*$p < 0.05$ Compared with the observation period (related two-group t-test or Wilcoxon's signed rank sum test)
$p < 0.05$ Compared with the placebo group (independent two-group t-test)
[a]$p = 0.081$ Compared with the placebo group (independent two-group t-test)
[b]$p = 0.070$ Compared with the placebo group (Wilcoxon's signed rank sum test)

Example 16

Test on an Inhibitory Action on the Production of a Putrefaction Product

A placebo-controlled double-blind parallel-group comparison test was conducted, in which 39 healthy female subjects aged twenties to seventies were divided into two groups so that both groups were equalized in terms of age, height, body weight, and BMI, and after four weeks of observation period, ingested one pack (100 mL) of either the fermented milk product of Example 6 (test group) or a placebo drink (unfermented milk without bacteria, galactooligosaccharide, and polydextrose, a placebo group) daily for four weeks. In the final week of the observation period and the ingestion period, the blood was collected from the arms of the subjects. It is to be noted that the subjects were prohibited from ingesting any fermented milk products or probiotic products other than the present fermented milk or the placebo drink during the test period. Also, the bacterial count of the *Bifidobacterium* in the present fermented milk was $1 \times 10^8$ CFU/mL or more.

Serum was prepared from the blood thus collected in accordance with the ordinary method, which was stored frozen at −80° C. Then, 25 µL of the serum, 475 µL of milli-Q water, 200 µL of hydrochloric acid, and 10 µL of an internal standard solution (obtained by diluting 4-chlorophenol (Tokyo Chemical Industry Co., Ltd.) 300-fold with ethyl acetate (Sigma)) were stirred and mixed, and the resulting mixture was heated at 100° C. for 60 minutes in a sealed test tube. After cooling, 2 mL of diethyl ether was added to the resulting mixture: followed by stirring, and 1 mL of the resulting diethyl ether layer was collected and mixed with 1 mL of methanol containing 0.05 N sodium hydroxide. The resulting mixture was dried to be solidified with a centrifugal evaporator and then dissolved in 200 µL of ethyl acetate. The resulting mixture was filtered through a 0.45 µm filter (Ultrafree-MC, Millipore Corporation), whereby a HPLC sample was prepared. Also, 25 µL of a solution obtained by diluting para-cresol (Nacalai tesque, Inc.) to 0 to 0.01% with ethyl acetate, 675 µL of ethyl acetate, and 10 µL of the internal standard solution were mixed and provided as a standard solution. An HPLC analysis of para-cresol was conducted under the following conditions.

HPLC system: Alliance 2695 (Waters Corporation)

Detector: fluorescence detector Ex 260 nm, Ev 305 nm (using a 270 nm UV detector in combination)

Column: L-column 4.6×150 mm, a particle diameter of 5 µm (Chemical Evaluation and Research Institute)

Column temperature: 40° C.

Eluent: % A; 0.1% phosphoric acid, % B; acetonitrile, % A/% B=80/20 (isocratic)

Flow rate: 1.0 mL/min

Injection volume: 10 µL

Temperature of the sample chamber: 10° C.

Measurement time: 30 minutes

Although the blood para-cresol concentration after ingestion did not change compared with before ingestion in the placebo group, the concentration significantly decreased in the test group. Also, it was significantly lower in the test group compared with that in the placebo group (Table 16). It is to be noted that no adverse event associated with either the ingestion of the present fermented milk product or the placebo drink was observed during the test period.

TABLE 16

Blood para-cresol concentration before and after ingestion

|  | Before ingestion(µM) | After ingestion(µM) |
|---|---|---|
| Placebo group (n = 19) | 61.9 ± 16.7 | 67.0 ± 11.1 |
| Test group (n = 20) | 74.0 ± 13.0 | 34.3 ± 7.5*[#] |

*$p < 0.05$ Compared with before ingestion (related two-group t-test)
$p < 0.05$ Compared with the placebo group (independent two-group t-test)

The above results revealed that ingestion of the present fermented milk decreased the blood concentration of an intestinal putrefaction product (para-cresol), which was a biologically toxic substance produced by intestinal bacteria. This was considered to be a result of inhibition of the para-cresol production in the intestine owing to an intestinal environment-improving action. That is, the present fermented milk was considered to have an intestinal environment-improving action.

INDUSTRIAL APPLICABILITY

The method for producing bacteria belonging to the genus *Bifidobacterium* of the present invention enables acquisition of the bacteria belonging to the genus *Bifidobacterium* having excellent viability even under conditions with different environmental factors. This bacterial strain can be applied to various foods and drinks, and owing to its high viability in foods and drinks, the bacteria belonging to the genus *Bifidobacterium* can effectively exhibit their physiological functions. Also, a bacterial strain which is utilizable in various foods and drinks can be produced by improving the bacteria belonging to the genus *Bifidobacterium* having a specific physiological effect such as an anti-*Helicobacter pylori* bacteria action by the production method of the present invention; therefore, the present invention has extremely high industrial applicability.

What is claimed is:

1. A bacterium belonging to the genus *Bifidobacterium*, wherein the bacterium is *Bifidobacterium breve* YIT 12272 (FERM BP-11320).

2. A food or drink, comprising the bacterium of claim 1.

3. The food or drink of claim 2, which is a fermented food or drink.

4. The food or drink of claim 2, which is a fermented milk food or drink.

5. The food or drink of claim 2, further comprising a sweetener.

6. A method of making the food or drink of claim 2, comprising incorporating the *Bifidobacterium breve* YIT 12272 (FERM BP-11320) into a food or drink.

7. A method of making the food or drink of claim 3, comprising incorporating the *Bifidobacterium breve* YIT 12272 (FERM BP-11320) into a fermented food or drink.

8. A method of making the food or drink of claim 4, comprising incorporating the *Bifidobacterium breve* YIT 12272 (FERM BP-11320) into a fermented milk food or drink.

* * * * *

SEQUENCE LISTING

<160> NUMBER OF SEQ ID NOS: 30

<210> SEQ ID NO 1
<211> LENGTH: 19
<212> TYPE: DNA
<213> ORGANISM: Artificial sequence
<220> FEATURE:
<223> OTHER INFORMATION: Designed DNA based on Bifidobacterium gene

<400> SEQUENCE: 1
atggcaaaac cgggctgaa                                                19

<210> SEQ ID NO 2
<211> LENGTH: 16
<212> TYPE: DNA
<213> ORGANISM: Artificial sequence
<220> FEATURE:
<223> OTHER INFORMATION: Designed DNA based on Bifidobacterium gene

<400> SEQUENCE: 2
gcggatgaga ggtggg                                                   16

<210> SEQ ID NO 3
<211> LENGTH: 1151
<212> TYPE: DNA
<213> ORGANISM: Artificial sequence
<220> FEATURE:
<223> OTHER INFORMATION: Bifidobacterium breve YIT 12272

<400> SEQUENCE: 3
agccagtttc gaggtatggc cggtactacc acgcgaaccc gggcggtgga acagcctcca     60
aagggtgaag gtgttcatcg cttgcctccc gcgttgatgt cgtgaccgac ggctgcagca    120
gcgttggcgt cggcatccgg ctgatgcagc ctaccgtcct gcatcattac ggttcggcca    180
cagaagccag cgacgttggg atcgtgcgtt acgaccacta cggcagcgcc gttatcacgc    240
gctgcggcca tcaggatgcc catcacctca cgtccggtgg tctgatcgag ggcaccggtc    300
ggttcgtcgg cgaataccac ggctggtttc acgcgagcg cacgggcgat ggcgatgcgc     360
tgcatctgac cgccgctcat ctccccccggc cggttattgg cgagggcacg aaggcccatg    420
cgttccagcc agagaatcgc ggtgtcggtg gcggtgcggt atggcatgcc gtcgagcatc    480
atcggcagtg cgatattttc gactgccggc aattcgggaa gcagctggcc ggattggaag    540
acaaaaccga aagcgttgcg gcgcagcttg gtgcggccgg catcgctcat ggcatccaga    600
ttcgagccac ggaaggtcac tgtgccggcg gtcggcttga tgatgccggc gagcgcgtgc    660
agcagcgtgg acttgccgga ccagacgggc cccatgacag caaccgtctc accctcaccc    720
aatgcgaagc tcacgtggtt cagggcaagt gtgtgcatgg ttggcatggc aaaaccgggc    780
tgaacattgg cagcgggaac cgcagcacct gttccggccg gcatcacacc ggtaacgcca    840
tgaccggcct gcgcacgggc catactggcg gtgtagtcca tgatcaagtc atgtgcctcg    900
atcaccggag accactgctg ccgtgcgtcc tgttgttgca ctgcttccgg tgcggtctga    960
gtctgctgaa attgctgtgt tgctgtattc atactcccga gagtacggat cgagcagaag   1020
cctgaccatc aggctgcggt atgaaccttt tcaaccgccc cacccacctc tcatccgcaa   1080
ggattagaga ttcgcagtcg atgcgacaat acttttatca atggcaatgt ggataacttc   1140
ggaaactggc t                                                        1151

<210> SEQ ID NO 4
<211> LENGTH: 10

-continued

```
<212> TYPE: DNA
<213> ORGANISM: Artificial sequence
<220> FEATURE:
<223> OTHER INFORMATION: Random primer

<400> SEQUENCE: 4
gtgaagtagg                                                              10

<210> SEQ ID NO 5
<211> LENGTH: 10
<212> TYPE: DNA
<213> ORGANISM: Artificial sequence
<220> FEATURE:
<223> OTHER INFORMATION: Random primer

<400> SEQUENCE: 5
caatagccgt                                                              10

<210> SEQ ID NO 6
<211> LENGTH: 10
<212> TYPE: DNA
<213> ORGANISM: Artificial sequence
<220> FEATURE:
<223> OTHER INFORMATION: Random primer

<400> SEQUENCE: 6
cagtacccac                                                              10

<210> SEQ ID NO 7
<211> LENGTH: 10
<212> TYPE: DNA
<213> ORGANISM: Artificial sequence
<220> FEATURE:
<223> OTHER INFORMATION: Random primer

<400> SEQUENCE: 7
aggtaaccgt                                                              10

<210> SEQ ID NO 8
<211> LENGTH: 10
<212> TYPE: DNA
<213> ORGANISM: Artificial sequence
<220> FEATURE:
<223> OTHER INFORMATION: Random primer

<400> SEQUENCE: 8
cagtaccttc                                                              10

<210> SEQ ID NO 9
<211> LENGTH: 10
<212> TYPE: DNA
<213> ORGANISM: Artificial sequence
<220> FEATURE:
<223> OTHER INFORMATION: Random primer

<400> SEQUENCE: 9
ggttaaagcc                                                              10

<210> SEQ ID NO 10
<211> LENGTH: 10
<212> TYPE: DNA
<213> ORGANISM: Artificial sequence
<220> FEATURE:
<223> OTHER INFORMATION: Random primer

<400> SEQUENCE: 10
```
tcgacgatag                                                                  10

<210> SEQ ID NO 11
<211> LENGTH: 10
<212> TYPE: DNA
<213> ORGANISM: Artificial sequence
<220> FEATURE:
<223> OTHER INFORMATION: Random primer

<400> SEQUENCE: 11
agccaacgaa                                                                  10

<210> SEQ ID NO 12
<211> LENGTH: 10
<212> TYPE: DNA
<213> ORGANISM: Artificial sequence
<220> FEATURE:
<223> OTHER INFORMATION: Random primer

<400> SEQUENCE: 12
gttgcggtcc                                                                  10

<210> SEQ ID NO 13
<211> LENGTH: 10
<212> TYPE: DNA
<213> ORGANISM: Artificial sequence
<220> FEATURE:
<223> OTHER INFORMATION: Random primer

<400> SEQUENCE: 13
tgcgacttac                                                                  10

<210> SEQ ID NO 14
<211> LENGTH: 10
<212> TYPE: DNA
<213> ORGANISM: Artificial sequence
<220> FEATURE:
<223> OTHER INFORMATION: Random primer

<400> SEQUENCE: 14
gtagacaagc                                                                  10

<210> SEQ ID NO 15
<211> LENGTH: 10
<212> TYPE: DNA
<213> ORGANISM: Artificial sequence
<220> FEATURE:
<223> OTHER INFORMATION: Random primer

<400> SEQUENCE: 15
tgccgaattc                                                                  10

<210> SEQ ID NO 16
<211> LENGTH: 10
<212> TYPE: DNA
<213> ORGANISM: Artificial sequence
<220> FEATURE:
<223> OTHER INFORMATION: Random primer

<400> SEQUENCE: 16
cgaactagac                                                                  10

<210> SEQ ID NO 17
<211> LENGTH: 10
<212> TYPE: DNA
<213> ORGANISM: Artificial sequence

```
<220> FEATURE:
<223> OTHER INFORMATION: Random primer

<400> SEQUENCE: 17
ggcttaacac                                                                10

<210> SEQ ID NO 18
<211> LENGTH: 10
<212> TYPE: DNA
<213> ORGANISM: Artificial sequence
<220> FEATURE:
<223> OTHER INFORMATION: Random primer

<400> SEQUENCE: 18
aagactgtcc                                                                10

<210> SEQ ID NO 19
<211> LENGTH: 10
<212> TYPE: DNA
<213> ORGANISM: Artificial sequence
<220> FEATURE:
<223> OTHER INFORMATION: Random primer

<400> SEQUENCE: 19
gcggaaatag                                                                10

<210> SEQ ID NO 20
<211> LENGTH: 10
<212> TYPE: DNA
<213> ORGANISM: Artificial sequence
<220> FEATURE:
<223> OTHER INFORMATION: Random primer

<400> SEQUENCE: 20
ccgcagccaa                                                                10

<210> SEQ ID NO 21
<211> LENGTH: 10
<212> TYPE: DNA
<213> ORGANISM: Artificial sequence
<220> FEATURE:
<223> OTHER INFORMATION: Random primer

<400> SEQUENCE: 21
ccgatctaga                                                                10

<210> SEQ ID NO 22
<211> LENGTH: 10
<212> TYPE: DNA
<213> ORGANISM: Artificial sequence
<220> FEATURE:
<223> OTHER INFORMATION: Random primer

<400> SEQUENCE: 22
gaggacaaag                                                                10

<210> SEQ ID NO 23
<211> LENGTH: 10
<212> TYPE: DNA
<213> ORGANISM: Artificial sequence
<220> FEATURE:
<223> OTHER INFORMATION: Random primer

<400> SEQUENCE: 23
aacgcgcaac                                                                10
```

```
<210> SEQ ID NO 24
<211> LENGTH: 10
<212> TYPE: DNA
<213> ORGANISM: Artificial sequence
<220> FEATURE:
<223> OTHER INFORMATION: Random primer

<400> SEQUENCE: 24
gacgactatc                                                              10

<210> SEQ ID NO 25
<211> LENGTH: 10
<212> TYPE: DNA
<213> ORGANISM: Artificial sequence
<220> FEATURE:
<223> OTHER INFORMATION: Random primer

<400> SEQUENCE: 25
gtcaacgaag                                                              10

<210> SEQ ID NO 26
<211> LENGTH: 10
<212> TYPE: DNA
<213> ORGANISM: Artificial sequence
<220> FEATURE:
<223> OTHER INFORMATION: Random primer

<400> SEQUENCE: 26
agccagtttc                                                              10

<210> SEQ ID NO 27
<211> LENGTH: 10
<212> TYPE: DNA
<213> ORGANISM: Artificial sequence
<220> FEATURE:
<223> OTHER INFORMATION: Random primer

<400> SEQUENCE: 27
cgcataggtt                                                              10

<210> SEQ ID NO 28
<211> LENGTH: 10
<212> TYPE: DNA
<213> ORGANISM: Artificial sequence
<220> FEATURE:
<223> OTHER INFORMATION: Random primer

<400> SEQUENCE: 28
ggggttgacc                                                              10

<210> SEQ ID NO 29
<211> LENGTH: 10
<212> TYPE: DNA
<213> ORGANISM: Artificial sequence
<220> FEATURE:
<223> OTHER INFORMATION: Random primer

<400> SEQUENCE: 29
acttgcatcc                                                              10

<210> SEQ ID NO 30
<211> LENGTH: 10
<212> TYPE: DNA
<213> ORGANISM: Artificial sequence
<220> FEATURE:
<223> OTHER INFORMATION: Random primer
```

```
<400> SEQUENCE: 30
cccgtcagca                                                              10
```